(12) United States Patent
Timm

(10) Patent No.: US 11,540,977 B2
(45) Date of Patent: Jan. 3, 2023

(54) INJECTION APPARATUS AND METHOD OF USE

(71) Applicant: MOBIUS THERAPEUTICS, INC., St. Louis, MO (US)

(72) Inventor: Edward J. Timm, St. Louis, MO (US)

(73) Assignee: Mobius Therapeutics, LLC, St. Louis, MO (US)

(*) Notice: Subject to any disclaimer, the term of this patent is extended or adjusted under 35 U.S.C. 154(b) by 0 days.

(21) Appl. No.: 17/704,911

(22) Filed: Mar. 25, 2022

(65) Prior Publication Data
US 2022/0211581 A1 Jul. 7, 2022

Related U.S. Application Data

(63) Continuation of application No. PCT/US2021/064095, filed on Dec. 17, 2021.

(60) Provisional application No. 63/126,660, filed on Dec. 17, 2020.

(51) Int. Cl.
A61J 1/20 (2006.01)
A61F 9/00 (2006.01)
A61P 27/06 (2006.01)
A61J 1/14 (2006.01)
A61K 31/407 (2006.01)

(52) U.S. Cl.
CPC ........... A61J 1/2096 (2013.01); A61F 9/0008 (2013.01); A61J 1/1406 (2013.01); A61J 1/201 (2015.05); A61J 1/2037 (2015.05); A61J 1/2048 (2015.05); A61K 31/407 (2013.01); A61P 27/06 (2018.01)

(58) Field of Classification Search
CPC ........ A61J 1/2096; A61J 1/201; A61J 1/2037; A61J 1/2048; A61J 1/1406; A61F 9/0008; A61K 31/407; A61P 27/06
See application file for complete search history.

(56) References Cited

U.S. PATENT DOCUMENTS

| | | | |
|---|---|---|---|
| 7,743,799 B2 | 6/2010 | Mosler et al. | |
| 2007/0260176 A1* | 11/2007 | Tennican | A61M 5/284 604/88 |
| 2011/0004170 A1* | 1/2011 | Timm | A61P 27/02 604/416 |
| 2012/0323208 A1* | 12/2012 | Bochenko | A61J 1/2096 604/404 |
| 2013/0102657 A1 | 4/2013 | Hunter et al. | |
| 2015/0068640 A1 | 3/2015 | Garfield et al. | |
| 2018/0042765 A1* | 2/2018 | Noronha | A61F 9/0008 |
| 2019/0046410 A1* | 2/2019 | Shemesh | A61J 1/10 |

OTHER PUBLICATIONS

International Search Report and Written Opinion regarding International Application No. PCT/US2021/064095 dated Mar. 2, 2022, 8 pages.

* cited by examiner

Primary Examiner — Ariana Zimbouski
(74) Attorney, Agent, or Firm — Polsinelli PC

(57) ABSTRACT

The present disclosure relates to a system and kit for preparing a reconstitutable cytotoxic pharmaceutical formulation within a closed system to prevent unintended contact with or release of the cytotoxic pharmaceutical formulation. A safety connector and a vial adapter are provided, which include check valves that prevent the unintended release of the cytotoxic pharmaceutical formulation. Also disclosed herein are methods of using the system and kit.

26 Claims, 19 Drawing Sheets

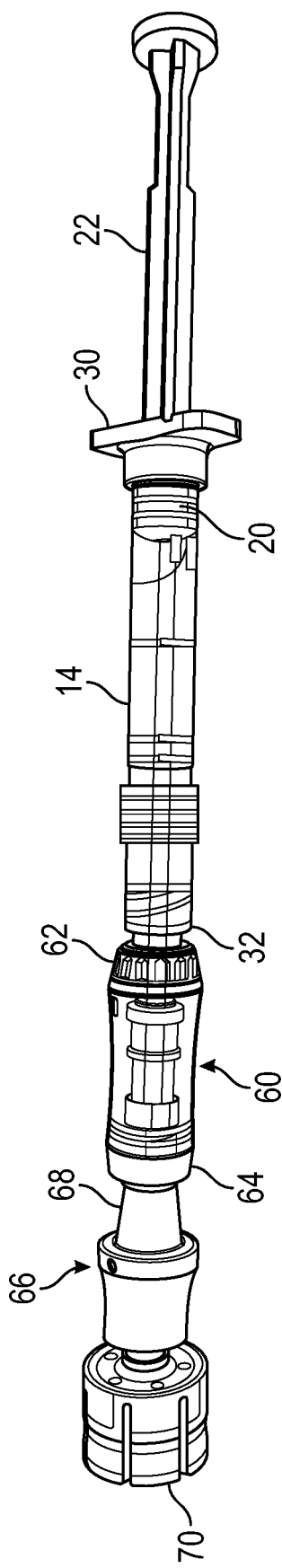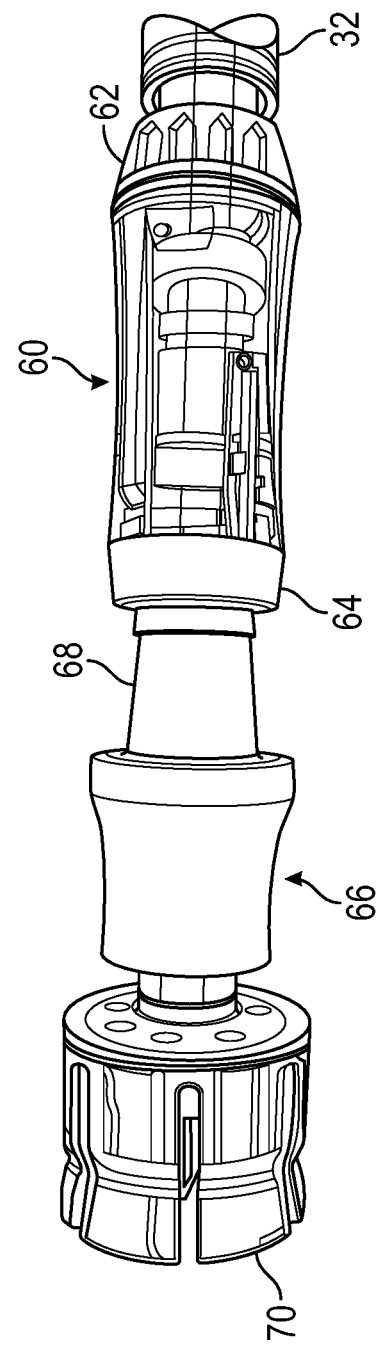
FIG. 5A
FIG. 5B

INJECTION APPARATUS AND METHOD OF USE

CROSS REFERENCE TO RELATED APPLICATIONS

The present application is a continuation of PCT Application No. PCT/US2021/064095, filed Dec. 17, 2021, which claims priority to U.S. Application Ser. No. 63/126,660, filed Dec. 17, 2020, the entire contents of which are herein incorporated in the present application by reference.

FIELD OF THE DISCLOSURE

The present invention relates generally to injection apparatus and kits, and method of use thereof, and more particularly to injection apparatus and methods for both preparing and administering a pharmaceutical agent to a subject.

BACKGROUND

Glaucoma is a disease resulting in loss of visual field and ultimately blindness. Its most common symptom is elevated intraocular pressure (IOP), which can be treated by lowering or controlling IOP through prescription eye drops, oral medications, laser treatment, surgery or a combination of these. For glaucoma surgery, trabeculectomy with adjunctive mitomycin C (MMC) treatment is the gold standard when a significant sustained reduction in IOP is needed. At the same time, finding the optimal technique and tools for application of MMC has remained a challenge. Mitomycin-C is an alkylating, anti-tumor antimetabolite used in ophthalmic surgery for its ability to inhibit fibroblast proliferation and suppress vascular ingrowth. Due to its cytotoxic nature, the packaging, dosage, route of delivery, application time and area of tissue exposure must all be controlled carefully to minimize the risk of complications following MMC administration. Possible serious complications include severe inflammation, endothelial cell damage, endothelial cell loss, and hypotony. A significant need remains for reliable, less-irritating, yet sterile delivery apparatus and methods for ophthalmological applications of MMC and other similarly cytotoxic pharmaceutical agents.

SUMMARY OF THE DISCLOSURE

Provided herein is a method of preparing a cytotoxic formulation for administration to a tissue. The method includes providing a sterile, closed system that includes: a sealed container of a single dose of a cytotoxic pharmaceutical agent in a reconstitutable form; a carrier containing a sterile liquid; a safety connector comprising a check valve, the safety connector permanently connected to the carrier; a vial adapter comprising a check valve, a vial end, and a syringe end, the vial adapter operable to removably connect to the sealed container via a spike at the vial end and connect to the safety connector at the syringe end; and a sterile syringe operable to connect to the vial adapter. The method further includes connecting the safety connector to the syringe end of the vial adapter, thereby opening the check valve in the safety connector and the check valve in the vial adapter; pushing the vial end of the vial adapter onto the sealed container, thereby piercing a lid of the sealed container with the spike; injecting the entire sterile water from the carrier into the vial, via the safety connector and the vial adapter; inverting the sealed container repeatedly to mix the cytotoxic pharmaceutical agent and sterile liquid to form a reconstituted cytotoxic formulation; disconnecting the vial adapter from the safety connector; connecting the sterile syringe to the vial adapter; and withdrawing a predetermined volume of the reconstituted cytotoxic formulation into the sterile syringe.

In some embodiments, the administration may be performed via injection. In some embodiments, the predetermined volume may be less than or equal to 1 mL. In some examples, the predetermined volume may be 0.1 mL. In some embodiments, the reconstituted cytotoxic formulation may have a concentration of about 0.01 mg/mL to about 1 mg/m L. In some examples, the reconstituted cytotoxic formulation may have a concentration of 0.2 mg/m L. In some embodiments, the pharmaceutical agent may include at least one antimetabolite agent. In some examples, the at least one antimetabolite agent may include mitomycin-C.

In some embodiments, the method may further include disconnecting the sterile syringe from the vial adapter; attaching a needle to the sterile syringe; and injecting the reconstituted cytotoxic formulation of the periocular tissue of a patient.

Further provided herein is a method of treating glaucoma. The method includes providing a sterile, closed system that includes: a sealed container of a single dose of a cytotoxic pharmaceutical agent in a reconstitutable form; a carrier containing a sterile liquid; a safety connector comprising a check valve, the safety connector permanently connected to the carrier; a vial adapter comprising a check valve, a vial end, and a syringe end, the vial adapter operable to removably connect to the sealed container via a spike at the vial end and connect to the safety connector at the syringe end; and a sterile syringe operable to connect to the vial adapter. The method further includes connecting the safety connector to the syringe end of the vial adapter, thereby opening the check valve in the safety connector and the check valve in the vial adapter; pushing the vial end of the vial adapter onto the sealed container, thereby piercing a lid of the sealed container with the spike; injecting the entire sterile water from the carrier into the vial, via the safety connector and the vial adapter; inverting the sealed container repeatedly to mix the cytotoxic pharmaceutical agent and sterile liquid to form a reconstituted cytotoxic formulation; disconnecting the vial adapter from the safety connector; connecting the sterile syringe to the vial adapter; withdrawing a predetermined volume of the reconstituted cytotoxic formulation into the sterile syringe; disconnecting the sterile syringe from the vial adapter; attaching a needle or cannula to the sterile syringe; and injecting the reconstituted cytotoxic formulation to the periocular tissue of a patient in need thereof.

In some embodiments, the administration may be performed via injection. In some embodiments, the predetermined volume may be less than or equal to 1 mL. In some examples, the predetermined volume may be 0.1 mL. In some embodiments, the reconstituted cytotoxic formulation may have a concentration of about 0.01 mg/mL to about 1 mg/m L. In some examples, the reconstituted cytotoxic formulation may have a concentration of 0.2 mg/m L. In some embodiments, the pharmaceutical agent may include at least one antimetabolite agent. In some examples, the at least one antimetabolite agent may include mitomycin-C.

Further provided herein is a method of treating glaucoma. The method includes preparing a reconstituted cytotoxic pharmaceutical formulation in a sterile, closed system; and administering a predetermined volume of the reconstituted cytotoxic pharmaceutical formulation to a patient in need thereof. In some embodiments, the sterile, closed system may include a sealed container of a single dose of a cytotoxic pharmaceutical agent in a reconstitutable form; a carrier containing a sterile liquid and connected to a safety connector, the safety connector comprising a check valve, the safety connector permanently connected to the carrier; a vial adapter comprising a check valve, a vial end, and a syringe end, the vial adapter operable to removably connect to the sealed container via a spike at the vial end and connect to the safety connector at the syringe end; and a sterile syringe operable to connect to the vial adapter.

In some embodiments, the administration may be performed via injection. In some embodiments, the predetermined volume may be less than or equal to 1 mL. In some examples, the predetermined volume may be 0.1 mL. In some embodiments, the reconstituted cytotoxic formulation may have a concentration of about 0.01 mg/mL to about 1 mg/m L. In some examples, the reconstituted cytotoxic formulation may have a concentration of 0.2 mg/m L. In some embodiments, the pharmaceutical agent may include at least one antimetabolite agent. In some examples, the at least one antimetabolite agent may include mitomycin-C.

BRIEF DESCRIPTION OF THE FIGURES

FIG. 3A shows the safety connector connected to the carrier prior to inserting the plunger rod. FIG. 3B shows the safety connector connected to the carrier after insertion of the plunger rood. FIG. 3C shows a view of the distal end of the safety connector. FIG. 3D shows an isometric view of the safety connector.

FIG. 4A shows a side view of the vial adapter. FIG. 4B shows an isometric view of the vial adapter, including the spike. FIG. 4C shows an isometric view of the carrier end of the vial adapter.

FIG. 5A shows the safety connector connected to both the vial adapter and to the carrier. FIG. 5B shows a close-up view of the safety connector connected to the vial adapter.

FIG. 6A shows an isometric view of the tray. FIG. 6B shows the tray with the safety connector affixed to the first cylindrical connector and the TB syringe connected to the second cylindrical connector for closed system venting. FIG. 6C shows a side-view of the tray with the safety connector affixed to the first cylindrical connector and the TB syringe connected to the second cylindrical connector.

DETAILED DESCRIPTION

Figure 1:
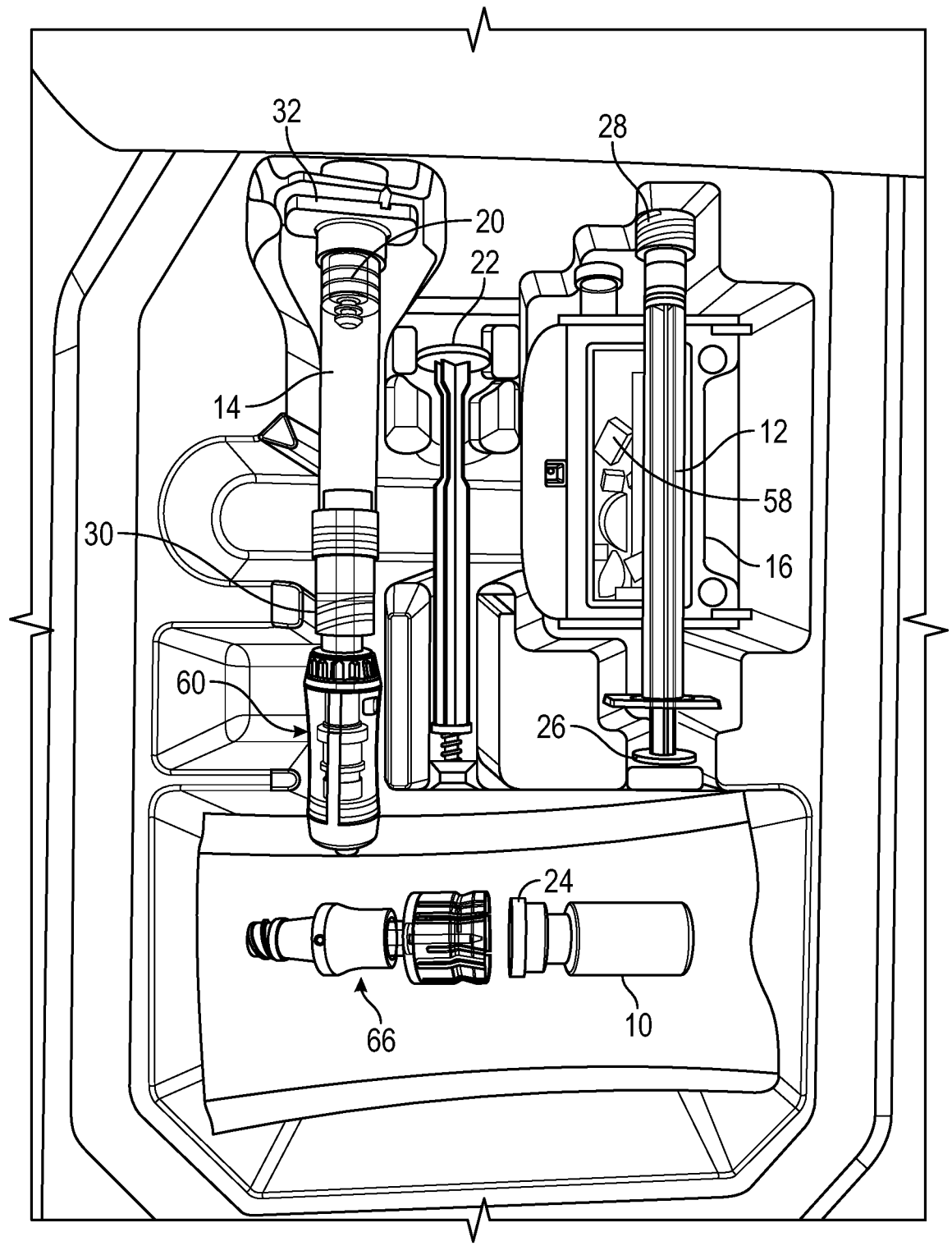
FIG. 1 shows an exemplary system of the present disclosure provided in a kit.

Before the present invention is disclosed and described, it is to be understood that this invention is not limited to the particular methods, compositions, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

Concentrations, amounts, and other numerical data may be expressed or presented herein in a range format. It is to be understood that such a range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 2 to about 50" should be interpreted to include not only the explicitly recited values of 2 to 50, but also include all individual values and sub-ranges within the indicated range. Thus, included in this numerical range are individual values such as 2, 2.4, 3, 3.7, 4, 5.5, 10, 10.1, 14, 15, 15.98, 20, 20.13, 23, 25.06, 30, 35.1, 38.0, 40, 44, 44.6, 45, 48, and sub-ranges such as from 1-3, from 2-4, from 5-10, from 5-20, from 5-25, from 5-30, from 5-35, from 5-40, from 5-50, from 2-10, from 2-20, from 2-30, from 2-40, from 2-50, etc. This same principle applies to ranges reciting only one numerical value as a minimum or a maximum. Furthermore, such an interpretation should apply regardless of the breadth of the range or the characteristics being described.

As used herein, the term "about" is used to provide flexibility to a numerical range endpoint by providing that a given value may be "a little above" or "a little below" the endpoint. For example, the endpoint may be within 10%, 8%, 5%, 3%, 2%, or 1% of the listed value. Further, for the sake of convenience and brevity, a numerical range of "about 50 mg/mL to about 80 mg/m L" should also be understood to provide support for the range of "50 mg/mL to 80 mg/m L." The endpoint may also be based on the variability allowed by an appropriate regulatory body, such as the FDA, USP, etc.

In this disclosure, "comprises," "comprising," "containing," and "having" and the like can have the meaning ascribed to them in U.S. Patent Law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. In this specification when using an open ended term, like "comprising" or "including," it is understood that direct support should be afforded also to "consisting essentially of" language as well as "consisting of" language as if stated explicitly and vice versa.

I. System

Provided herein is a system for reconstituting a cytotoxic pharmaceutical formulation. The system enables the safe and simplified preparation of a pharmaceutical agent such as mitomycin-C for transient application of the pharmaceutical agent. The preparation of the pharmaceutical agent takes place in a closed system to avoid unintended contact with the pharmaceutical agent or release of the pharmaceutical agent. Several of the component parts are known in the prior art in one form or another. Therefore, these component parts are not described in detail.

Referring now to FIG. 1, the system includes a sealed container 10 of the pharmaceutical agent, a syringe 12, a carrier 14, a safety connector 60, a vial adapter 66, and a mixing tray 16. As stated earlier, each of these component parts can be constructed of the materials typically used to manufacture similar parts.

The sealed container 10 has a construction that is known in the art. In some embodiments, the sealed container may contain cytotoxic agents such as antimetabolite agents. In some examples, the pharmaceutical agent may include mitomycin-C. More details regarding the pharmaceutical agents within the scope of the present disclosure are provided in Section IV below. In some embodiments, the sealed container 10 may be a pharmaceutical vial. The sealed container 10 has a top 24 that can be pierced by a spike provided on a vial adapter 66 of the present disclosure, which seals closed after the spike 72 is removed from the top 24 of the sealed container.

The sterile syringe 12 also has the typical construction of a syringe. In a preferred embodiment of the invention, the syringe 12 is a one cc syringe, such as a tuberculin syringe (also referred to herein as a "TB syringe"). The sterile syringe 12 has a plunger 26 that is manually withdrawn from the body of the sterile syringe to produce a suction force at the distal tip 28 of the sterile syringe.

The carrier 14 also has the construction of any known carrier. In some embodiments, the carrier 14 may be a syringe. In embodiments where the carrier is a syringe, the carrier may be referred to as a "first syringe" and the sterile syringe may be referred to as the "second syringe." The carrier includes a sterile liquid. In a preferred embodiment, the sterile liquid is sterile water. In other embodiments, the sterile liquid is sterile saline. The amount of sterile liquid is provided to mix with the pharmaceutical agent contained by the sealed container 10 to reconstitute the pharmaceutical agent in the sealed container 10. The carrier 14 has a proximal end 30 that includes a safety connector 60 of the present disclosure described in more detail below The carrier distal end 32 includes a rubber plunger 20 adapted to receive a plunger rod 22 to push the sterile liquid out of the carrier 14. In some embodiments, the plunger rod 22 may have a threaded end that screws into the rubber plunger 20. The carrier 14 and the plunger rod 22 may be packaged disassembled.

Figure 2:
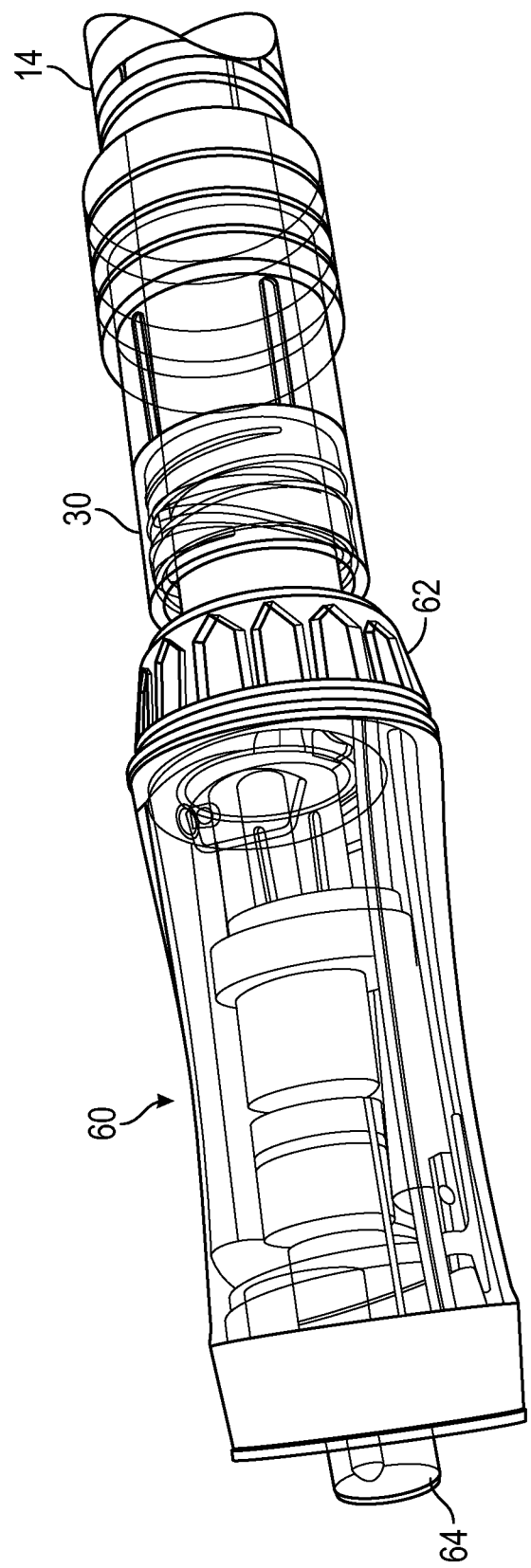
FIG. 2 shows an exemplary safety connector of the present disclosure.
Figure 3A:
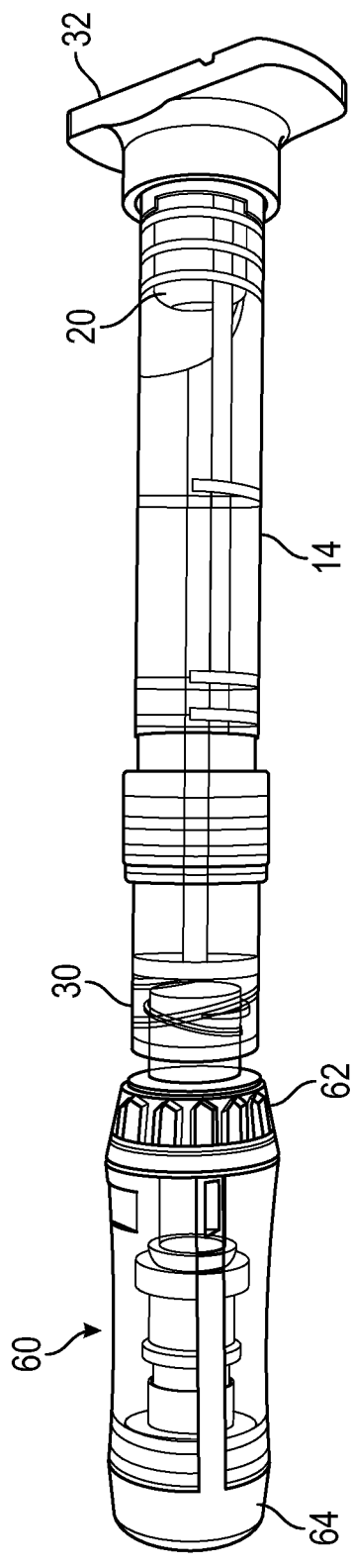
FIGS. 3A-3D show the safety connector connected to the carrier in various configurations.
Figure 3B:
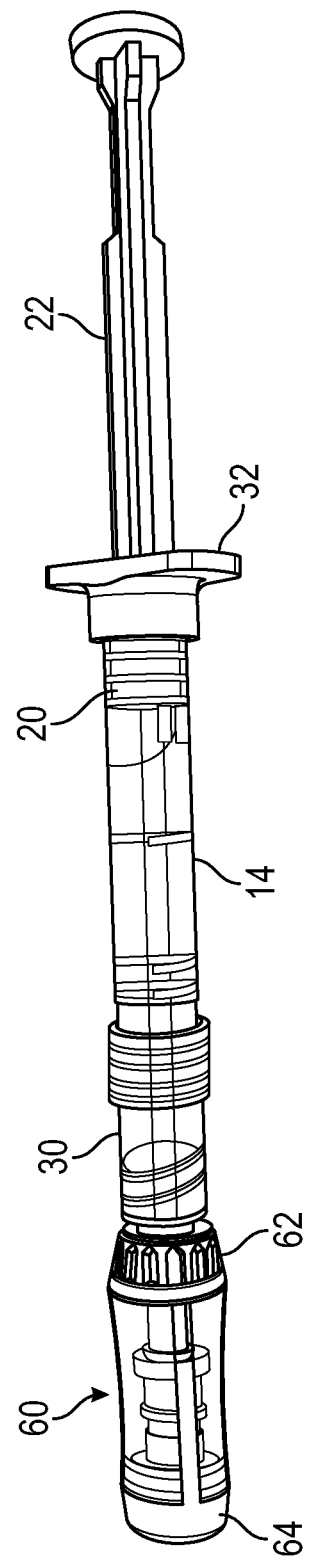
Figure 3C:
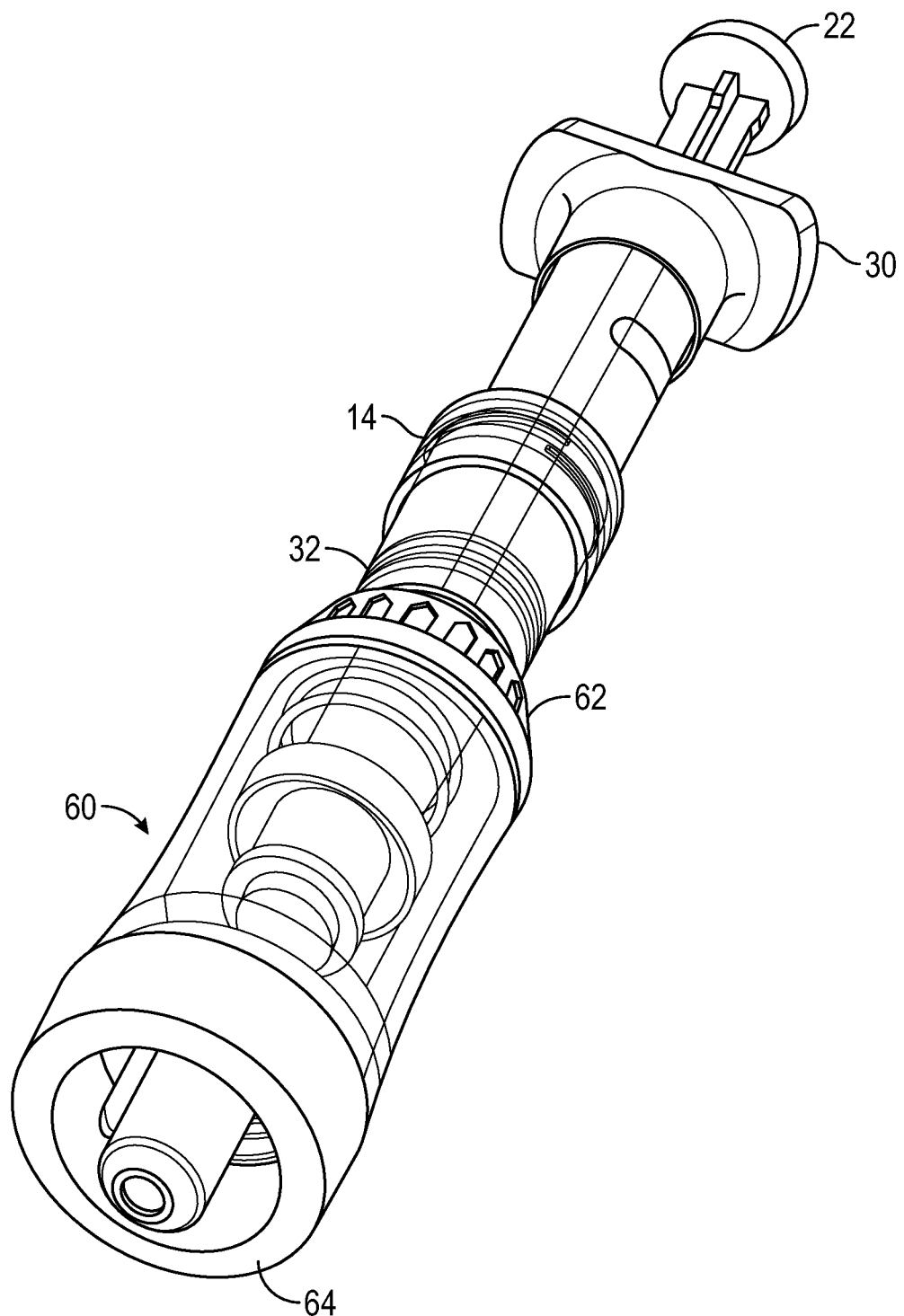
Figure 3D:
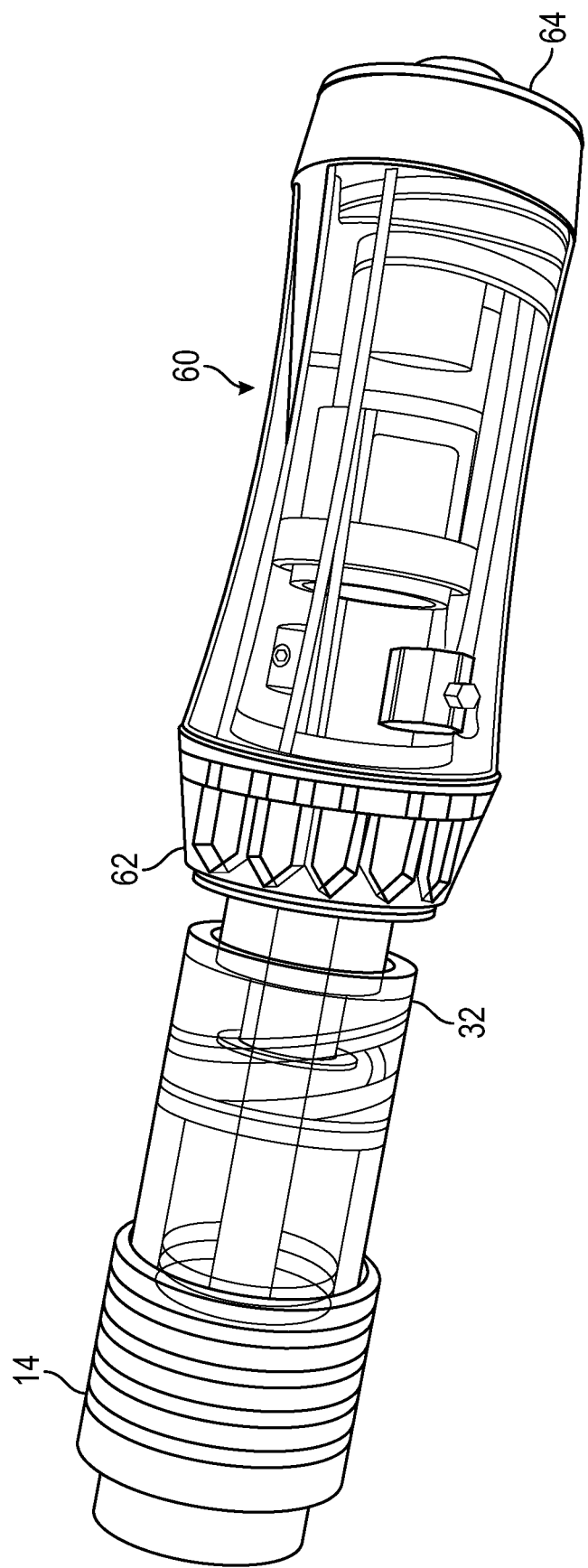

The system includes a safety connector 60, shown in FIG. 2. As shown in FIGS. 3A-3D, the safety connector 60 is connected to the distal end of the carrier 14. The safety connector 60 includes a carrier end 62 connected to the carrier 14, a distal end 64 operable to connect to the vial adapter 66 and the first cylindrical connector 50 of the tray, and a check valve that opens only when the safety connector 60 is properly connected to the vial adapter 66 or to the first cylindrical connector 50. When the safety connector is not connected to vial adapter 66 or the first cylindrical connector 50, the check valve remains in a closed position; thus, there is no flow in or out of the carrier 14. This ensures that the sterile liquid remains sterile during storage and prevents leaking both before and after reconstitution of the pharmaceutical agent. In some embodiments, the carrier end 62 of the safety connector 60 may be permanently connected to the proximal end 30 of the carrier 14. In other embodiments, the carrier end 62 of the safety connector 60 may be removably connected to the proximal end 30 of the carrier 14.

Figure 4A:
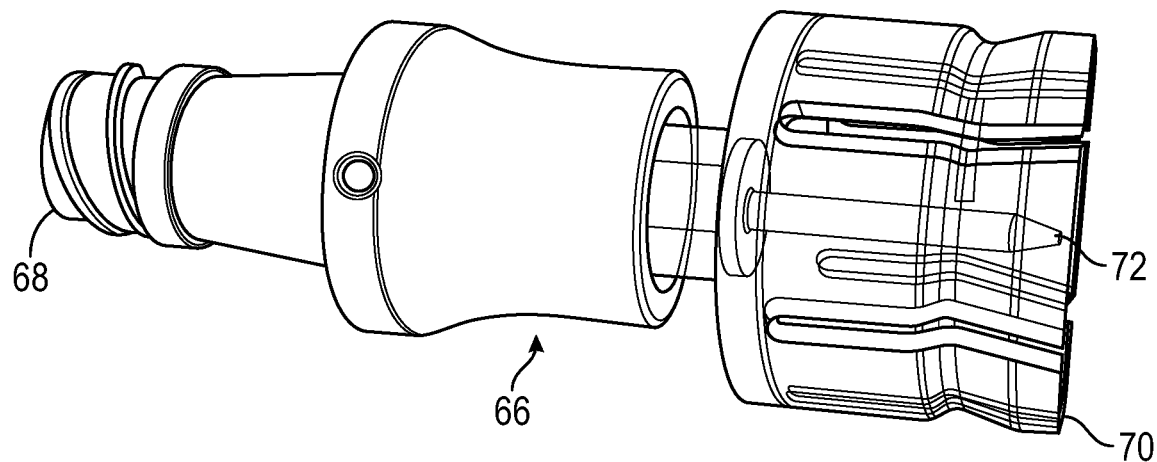
FIGS. 4A-4C show an exemplary vial adapter of the present disclosure.
Figure 4B:
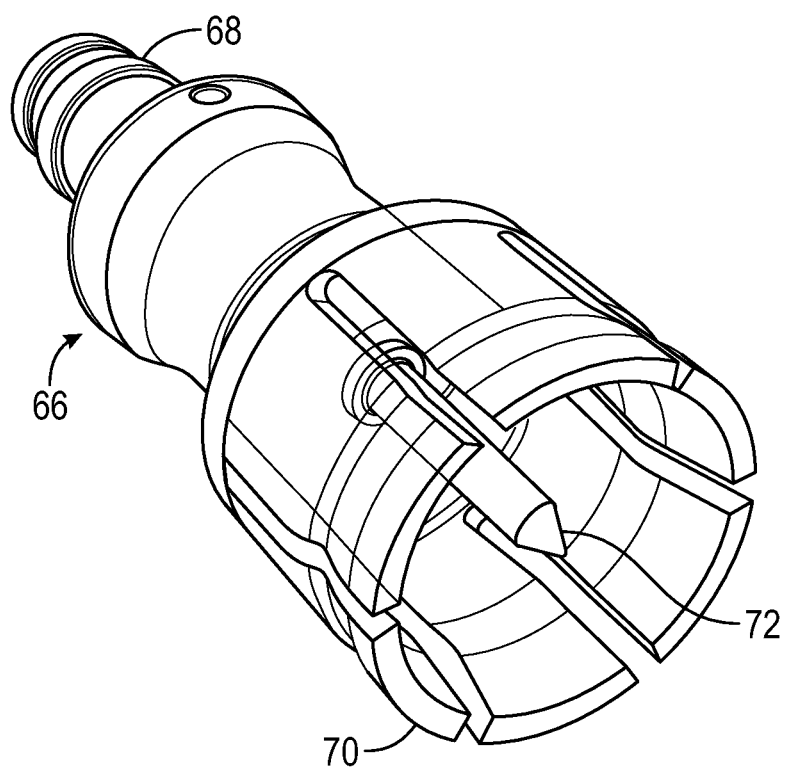
Figure 4C:
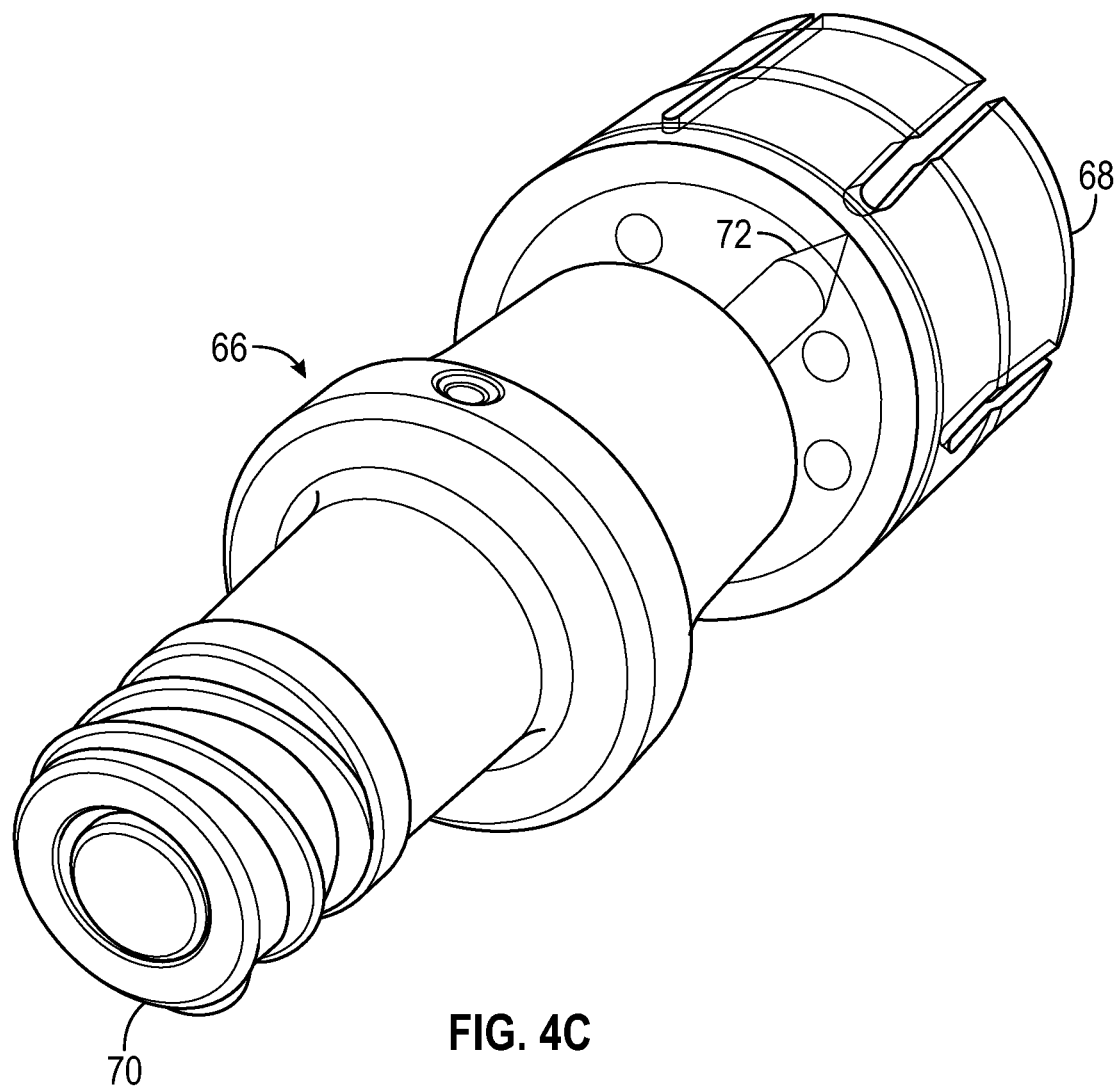

The system includes a vial adapter, shown in FIGS. 4A-4C. The vial adapter 66 is operable to reversibly connect to the safety connector 60 and to the sealed container 10. The vial adapter 66 includes a syringe end 68, a vial end 70, and a check valve that opens only when the vial adapter 66 is properly connected to the safety connector 60 and to the sealed container 10. The syringe end 68 of the vial adapter 66 may be operable to connect to the safety connector 60 and to the sterile syringe 12. The vial end 70 of the vial adapter 66 includes a spike 72 that is operable to pierce a membrane of the sealed container. When the vial adapter 66 is properly connected to the safety connector 60 and to the sealed container 10, as shown in FIGS. 5A-5B, the diluent in the carrier may be pushed through the carrier 14 into the sealed container 10 for reconstitution of the pharmaceutical agent. In some embodiments after reconstitution of the pharmaceutical agent, the pharmaceutical agent may be drawn back through the vial adapter 66 and the safety connector 60 into the carrier 14. In other embodiments after reconstitution of the pharmaceutical agent, the carrier 14 with the safety connector 60 may be disconnected from the syringe end 68 of the vial adapter 66, the safety syringe 12 may be connected to the syringe end 68 of the vial adapter 66, and a volume of the reconstituted pharmaceutical agent may be drawn into the sterile syringe 12.

Figure 6A:
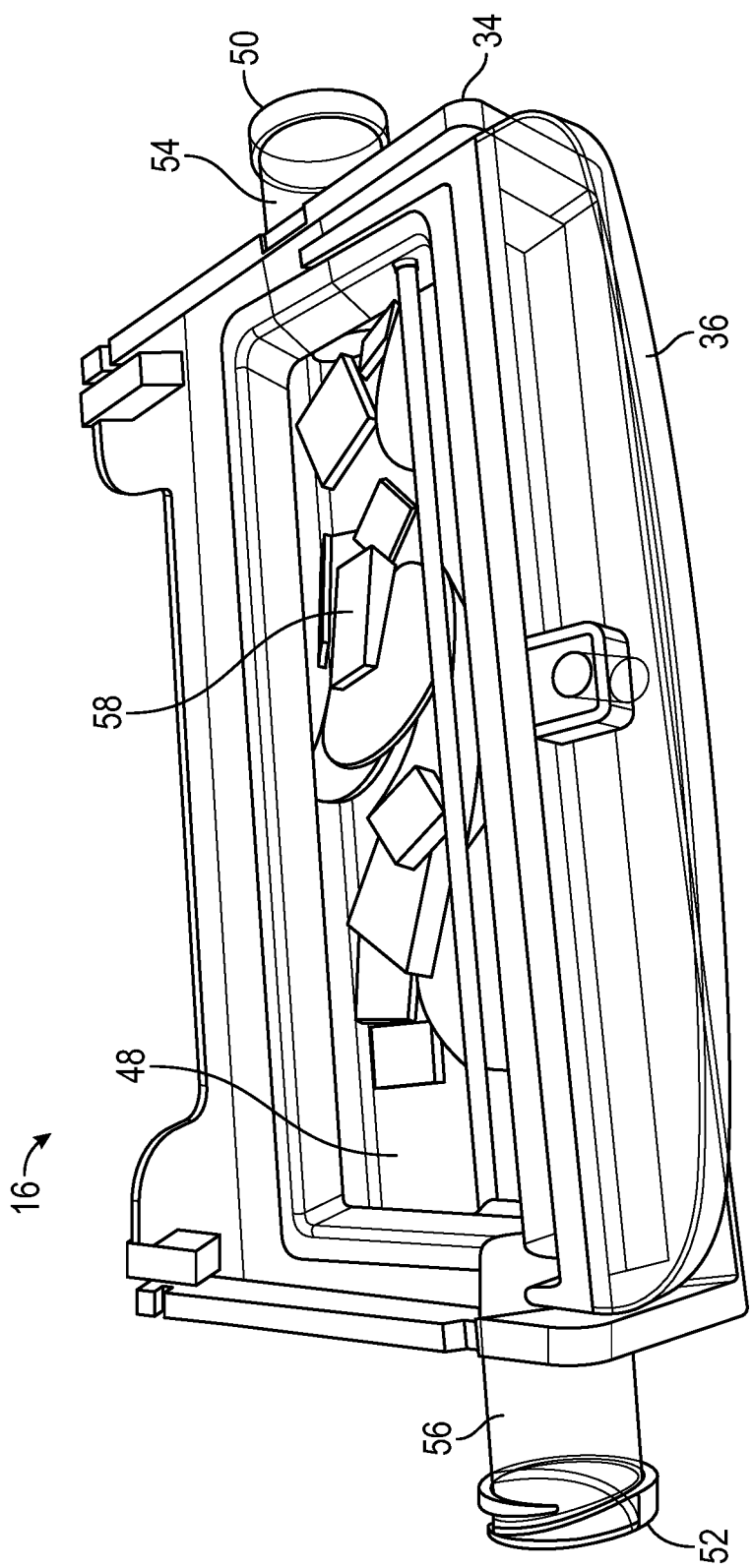
FIGS. 6A-6C show the tray containing sterile, absorbent pads of the present disclosure.
Figure 6B:
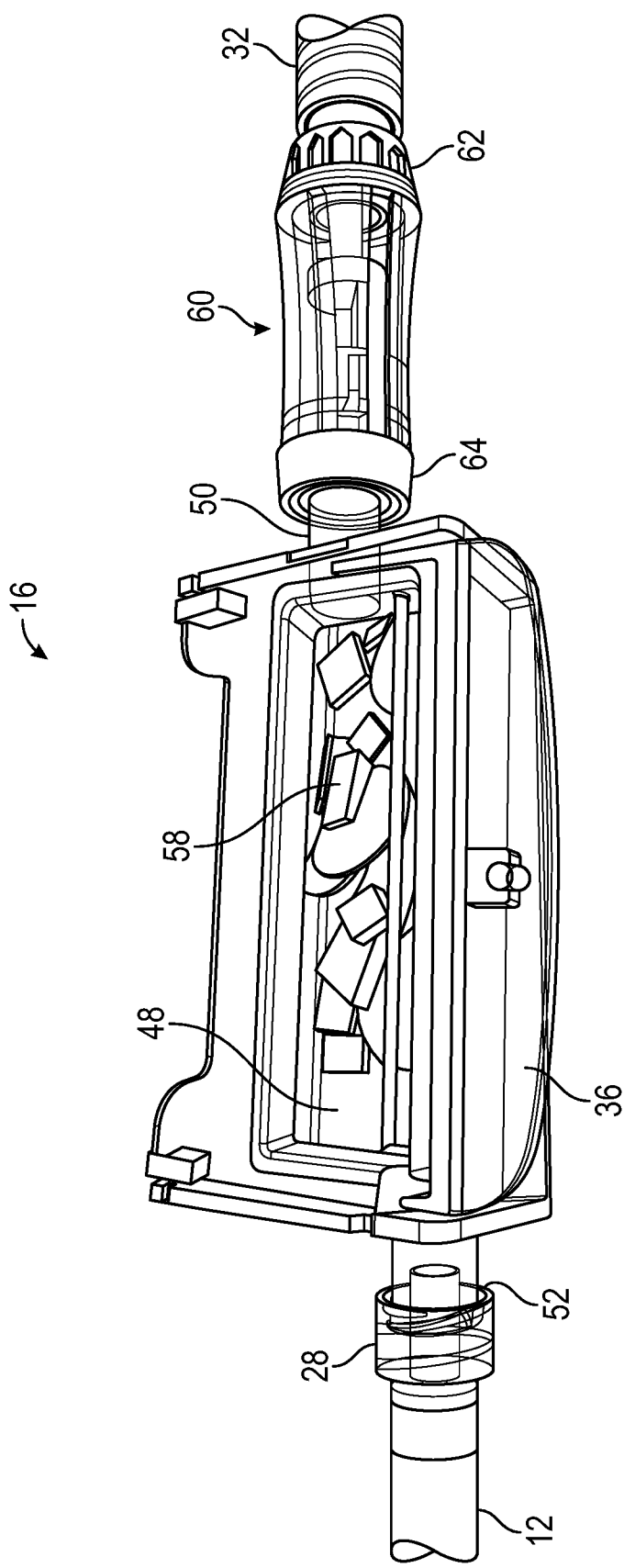
Figure 6C:
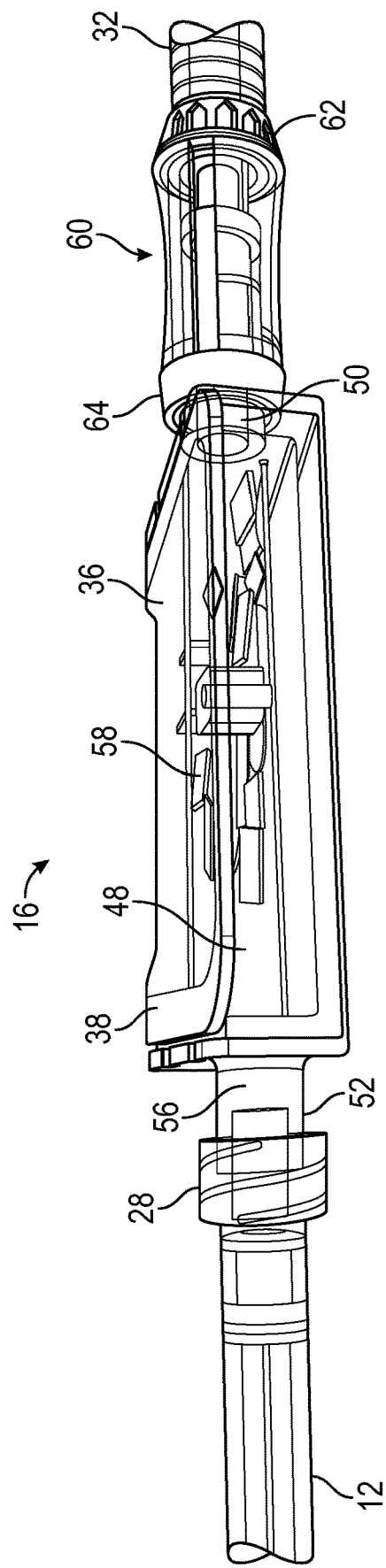

The system includes a tray 16 shown in FIGS. 6A-6C. The tray is comprised of a tray body 34 and a tray cover 36. Preferably the materials of the body 34 and cover 36 are substantially clear, inert plastic materials that may be employed in containing a pharmaceutical agent such as mitomycin-C.

The tray body 34 has a rectangular block configuration with opposite top 38 and bottom exterior surfaces, and a plurality of side exterior surfaces. A pair of arms project outwardly from one of the tray side surfaces 42. The arms 44 have axially aligned post holes that function as pivot connections for the cover 36. The cover 36 is operable to open and close.

A compartment 48 is recessed into the top surface 38 of the tray. As shown in the drawing figures, the compartment 48 has a rectangular configuration and defines an interior compartment having an interior volume between the tray top 38 and bottom surfaces, and the tray side surfaces 42. The interior volume of the compartment 48 is accessible through the top opening of the cavity in the tray top surface 38. The interior volume of the compartment 48 is properly sized to accommodate the combined volume of sponges 58 and the quantity of diluent in the carrier 14.

A pair of first 50 and second 52 cylindrical connectors project outwardly from opposite side surfaces of the tray 34. The first connector 50 has a first interior passage 54 that extends through the connector 50 and through the tray 34. The first passage 54 communicates the exterior environment of the tray with the tray compartment 48. The first cylindrical connector 50 is operable to removably connect to the safety connector 60. When the safety connector 60 is connected to the first cylindrical connector 50, the first passage 54 is in communication with the carrier 14 and the safety connector 60. The second connector 52 has a second interior passage 56 that extends through the connector and the tray 34. The second passage 56 also communicates the exterior environment of the tray 34 with the tray compartment 48. The second cylindrical connector 52 is operable to reversibly connect to the sterile syringe 12. The first passage 54 and the second passage 56 are separate from each other and are separate from the top opening of the compartment 48.

The sterile syringe 12 is operable to connect to the second cylindrical connector 52 of the tray 34 and/or to the syringe end 68 of the vial adapter 66. When connected to the second cylindrical connector 52, the sterile syringe 12 is operable to aspirate air and/or liquid from the tray compartment 48 by a suction force. When connected to the syringe end 68 of the vial adapter 66, the sterile syringe 12 is operable to withdraw a volume of the reconstituted pharmaceutical agent from the sealed container 10. The volume may be a predetermined volume selected from 0.1 mL, 0.2 mL, 0.3 mL, 0.4 mL, 0.5 mL, 0.6 mL, 0.7 mL, 0.8 mL, 0.9 mL, or 1 mL. In some embodiments, the full volume of the reconstituted pharmaceutical agent in the vial may not be withdrawn into the sterile syringe.

The tray compartment 48 has an interior volume that is dimensioned to receive and accommodate one or more sterile absorbent pads or sponges 58 in the compartment 48. In the preferred embodiment, the sterile absorbent pads or sponges 58 are constructed of an absorbent material that is known in the art and is used for the transient application of a pharmaceutical agent such as mitomycin-C. An example of such a pad is a Weck-Cel™™ type surgical sponge provided by Medtronic Xomed, Inc. The sterile absorbent pads or sponges are pre-cut into multiple shapes and sizes so that the surgeon or other healthcare professional can select the appropriate pad or sponge for his or her patient. In a preferred embodiment, the sterile absorbent pads or sponges range from 1-10 mm, 2-8 mm, and preferably 3 mm to 6 mm in size, and come in an array of shapes such as rectangles, circles, squares, and half-moons. Providing the array of pre-cut, sterile pads or sponges enables the medical professional to keep the treatment area clean and to select the size or shape of pad or sponge most appropriate for the treatment area. Furthermore, because the sterile absorbent pads or sponges are pre-cut, this eliminates the incidence of sponge fragmentation, preventing safety issues associated with this problem. Additionally, the volume of the fluid in the carrier 14 may be matched with the volume of the pads or sponges, which leads to a reliable and repeatable volume of drug being delivered to the operative site.

II. Kit

Further provided herein is a kit for preparing a cytotoxic formulation for administration to a tissue. An exemplary kit of the present disclosure is shown in FIG. 1. The components of the system of the present disclosure may be provided in a kit. The kit includes a sealed container of a single dose of a cytotoxic pharmaceutical agent in a reconstitutable form, a carrier containing a sterile liquid, a safety connector, a vial adapter, and a sterile packaging container. The carrier, safety connector, and the vial adapter are described in more detail in Section I. The pharmaceutical agent in a reconstitutable form is described in more detail in Section IV. In some embodiments, the kit may further include a tray, described in more detail in Section I. In some additional embodiments, the kit may further include a sterile syringe, described in more detail in Section I. In still further embodiments, the kit may further include a syringe plunger.

The sterile packaging container includes an internal volume. The internal volume is sealed such that the contents of the internal volume and the environment of the internal volume remain sterile. The internal volume houses the sealed container, the carrier connected to the safety connector, and the vial adapter. In some embodiments, the kit may include an instruction slip for user direction. The instruction slip may include diagrams, photographs, text, etc. to properly instruct a user on how to safely use the system of the present disclosure.

In some embodiments, the kit may include a waste container. The waste container may be suitable for disposal of medical waste, biohazardous waste, and/or chemical waste. In some aspects, the waste container may be a bag. In a preferred embodiment, the waste container is a chemotherapy waste disposal bag.

In some embodiments, the kit may include a non-sterile outer packaging container. The non-sterile outer packaging container may include a box or a bin. In some embodiments, the non-sterile outer packaging container may have a peel-away lid. The non-sterile outer packaging container allows for non-sterile handling of the kit prior to the kit's use. In some embodiments, the non-sterile outer packaging may have a sterile internal volume.

In an embodiment, the kit may be used to prepare a sterile cytotoxic formulation for administration to a tissue using the absorbent pads or via injection using the sterile syringe. The kit provides the benefit versatility to a surgeon, such that either method of administration is available from a single kit. In some embodiments, the selection of using the absorbent pads or the injection may depend on the specific patient, experience of the surgeon, or other varying conditions. Having a kit that can be used in two separate ways reduces both manufacturing costs and cost to the user.

III. Method

Further provided herein is a method of preparing a cytotoxic formulation for administration to a tissue. The method includes providing a sterile, closed system described in Section I. The method further includes connecting the safety connector to the syringe end of the vial adapter, thereby opening the check valve in the safety connector and the check valve in the vial adapter; pushing the vial end of the vial adapter onto the sealed container thereby piercing a lid of the sealed container with the spike; injecting the entire sterile diluent from the carrier into the vial via the safety connector and the vial adapter; inverting the sealed container repeatedly to mix the cytotoxic pharmaceutical agent and the sterile liquid to form a reconstituted cytotoxic formulation; withdrawing a volume of the cytotoxic formulation back into the carrier; and disconnecting the safety connector from the vial adapter, thereby closing the check valve in the safety connector and closing the check valve in the vial adapter, wherein the safety connector remains connected to the carrier and the vial adapter remains connected to the sealed container. In some embodiments, the pharmaceutical agent may be mitomycin-C. The method may further include disposing of one or more of the components of the system after use in a waste container, and then subsequently disposing of the waste container.

In some embodiments, the method may further include shaking the sealed container after the inverting and before the withdrawing to ensure all of the pharmaceutical agent is reconstituted.

In some embodiments, the method may further include letting the sealed container stand at room temperature after the inverting and before the withdrawing to allow all of the product to dissolve.

In some embodiments, the concentration of the cytotoxic formulation withdrawn into the carrier may be at least about 0.01 mg/mL. In some additional embodiments, the concentration of the cytotoxic formulation withdrawn into the carrier may be at least about 0.01 mg/mL to at least about 1 mg/mL. In some aspects, the concentration of the cytotoxic formulation withdrawn into the carrier may be at least about 0.01 mg/mL, 0.02 mg/mL, 0.03 mg/mL, 0.04 mg/mL, 0.05 mg/mL, 0.06 mg/mL, 0.07 mg/mL, 0.08 mg/mL, 0.09 mg/mL 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, or at least about 1 mg/mL. In a preferred embodiment wherein the pharmaceutical agent is mitomycin-C, the concentration of the cytotoxic formulation withdrawn into the carrier is at least about 0.1 mg/mL mitomycin-C.

In some embodiments, the method may further include connecting the safety connector to a first cylindrical connector of a tray and connecting a sterile syringe to a second cylindrical connector of the tray. The tray and the components of the tray are described in more detail in Section I. The compartment of the tray may include at least one sterile, absorbent pad. In some additional embodiments, the method may further include injecting the volume of the cytotoxic formulation into the compartment of the tray, thereby saturating the at least one sterile, absorbent pad with the cytotoxic formulation, and withdrawing any excess cytotoxic formulation and/or air into the sterile syringe. In some aspects, the cytotoxic formulation may remain undisturbed in the tray for at least 60 seconds before withdrawing any excess cytotoxic formulation and/or air into the sterile syringe. In further embodiments, one or more of the sterile, absorbent pads may be removed from the compartment of the tray before connecting the safety connector and the sterile syringe to the first cylindrical connector and the second cylindrical connector, respectively.

Further provided herein is a method of administering a cytotoxic formulation to a tissue. The method includes preparing a cytotoxic formulation as described above, removing one or more saturated sterile, absorbent pads from the compartment of the tray, and then applying the one or more saturated sterile, absorbent pads to the tissue. In some embodiments, the safety connector and the sterile syringe may remain connected to the first cylindrical connector and the second cylindrical connector, respectively, when the one or more saturated sterile, absorbent pads are removed from the compartment of the tray. In some additional embodiments, the administration of the cytotoxic formulation occurs within one hour after the reconstitution of the pharmaceutical agent.

In some embodiments, the method further includes removing the one or more saturated sterile, absorbent pads from the tissue after a period of time. In some aspects, the period of time may be 30 seconds, 1 minute, 1.5 minutes, 2 minutes, 2.5 minutes, 3 minutes, or longer than 3 minutes. In a preferred embodiment, the period of time is 2 minutes.

In some embodiments the tissue may be periocular tissue. In some aspects, the periocular tissue may include an episcleral (sub-Tenon's) space. In embodiments when the tissue is periocular tissue, the method may further include performing a peritomy after removing the one or more saturated sterile, absorbent pads. In some aspects, the periocular tissue may receive at least 0.1 mL of the cytotoxic formulation via the one or more sterile, absorbent pads.

When the one or more absorbent pads are removed from the tissue, they may be returned to the tray compartment. The cover of the tray may then be moved to a closed position with the used absorbent pads inside. The tray, absorbent pads, safety connector, sterile syringe, and carrier may then be placed in the waste container for disposal. In some embodiments, safety connector and the sterile syringe are still connected to the tray when placed in the waste container to prevent release of the cytotoxic formulation.

Figure 8A:
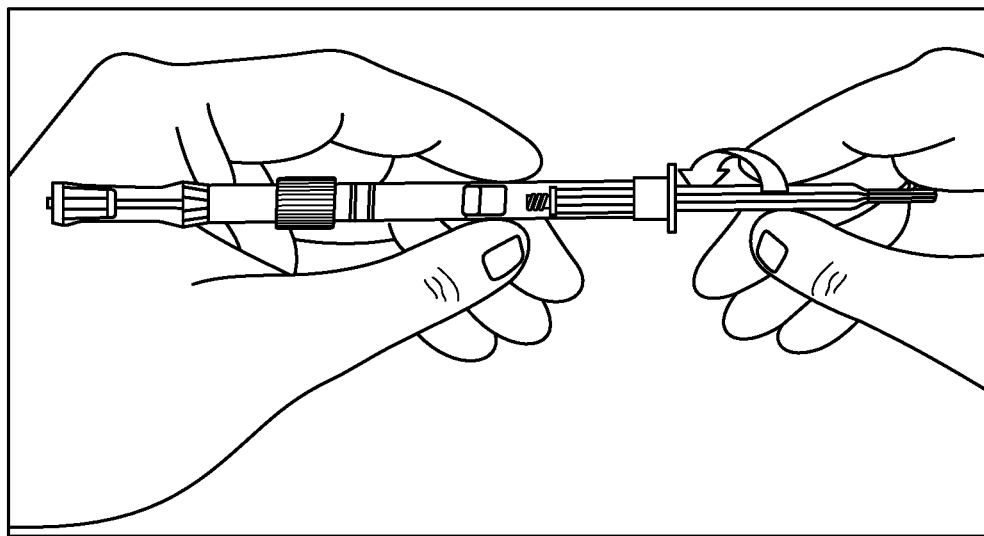
FIGS. 8A-8H show diagrams for using the system of the present disclosure to prepare a reconstituted pharmaceutical agent suitable for injection.
Figure 8B:
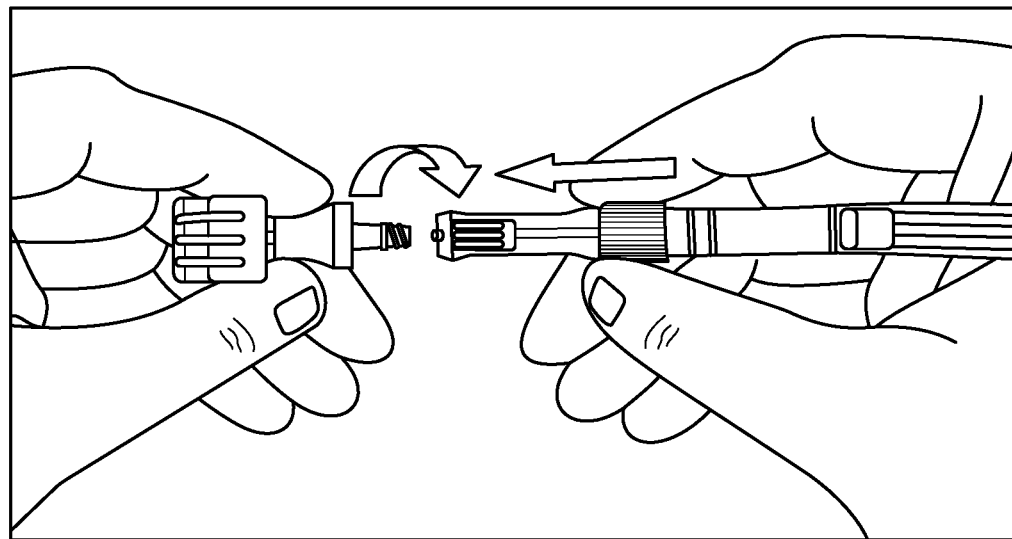
Figure 8C:
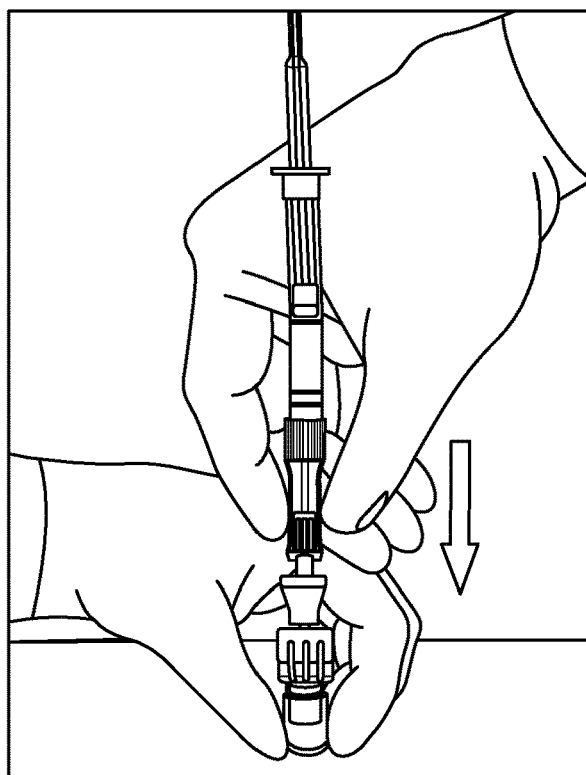
Figure 8D:
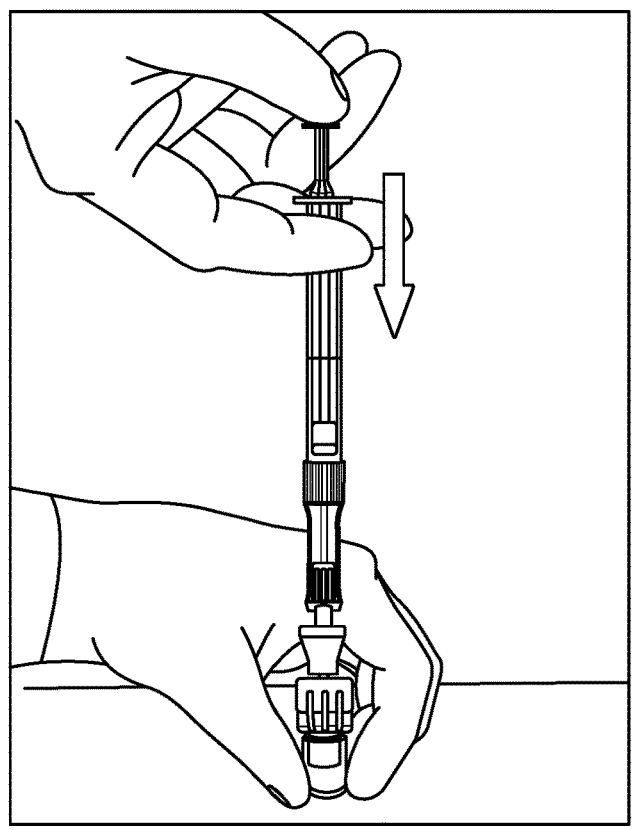
Figure 8E:
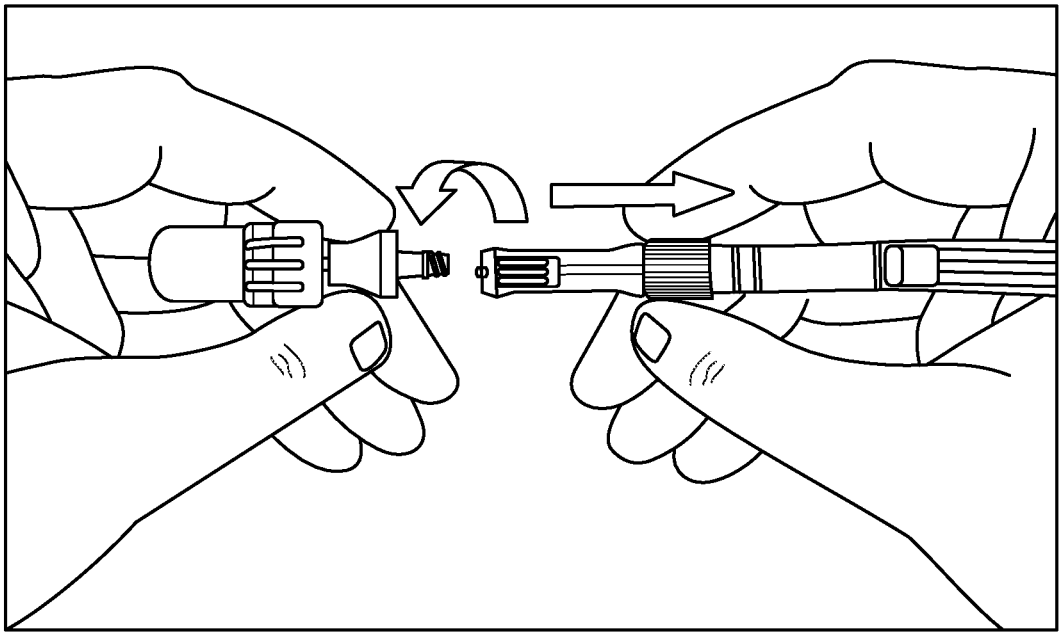
Figure 8F:
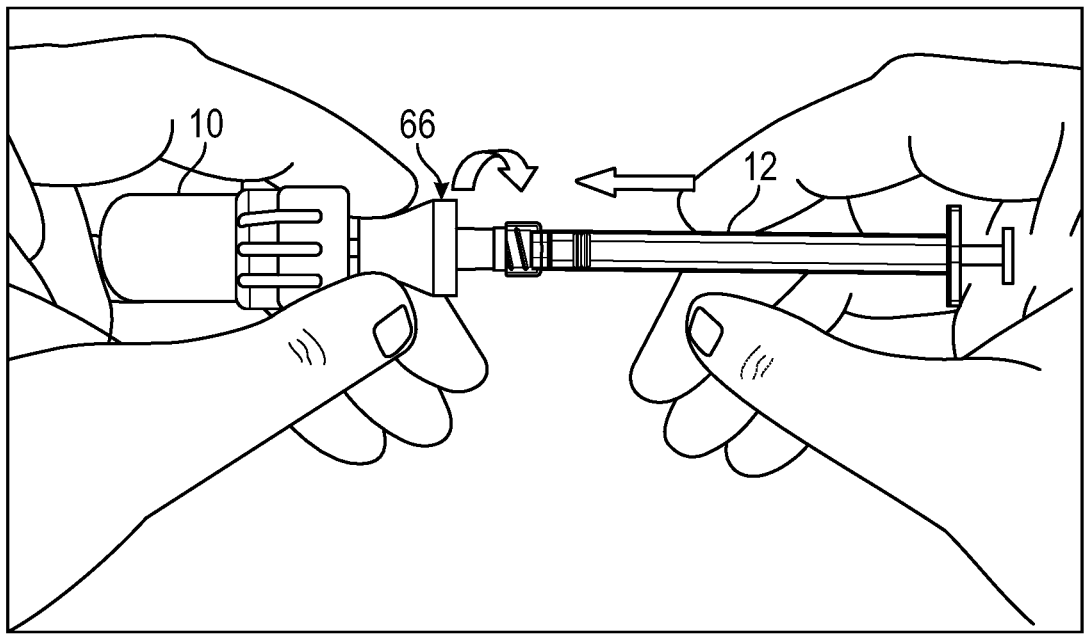
Figure 8G:
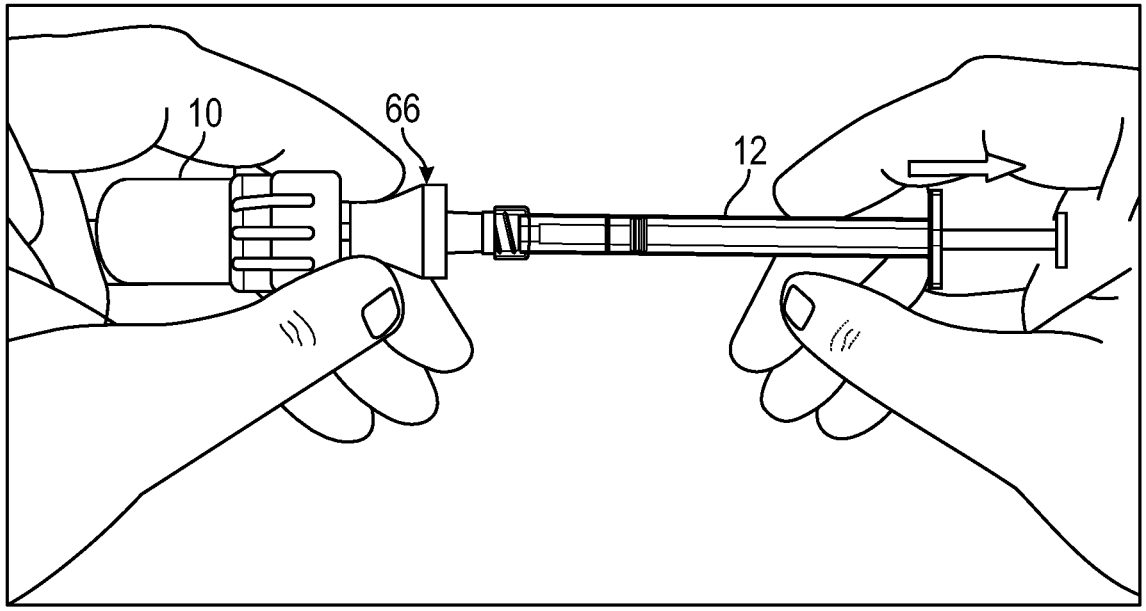
Figure 8H:
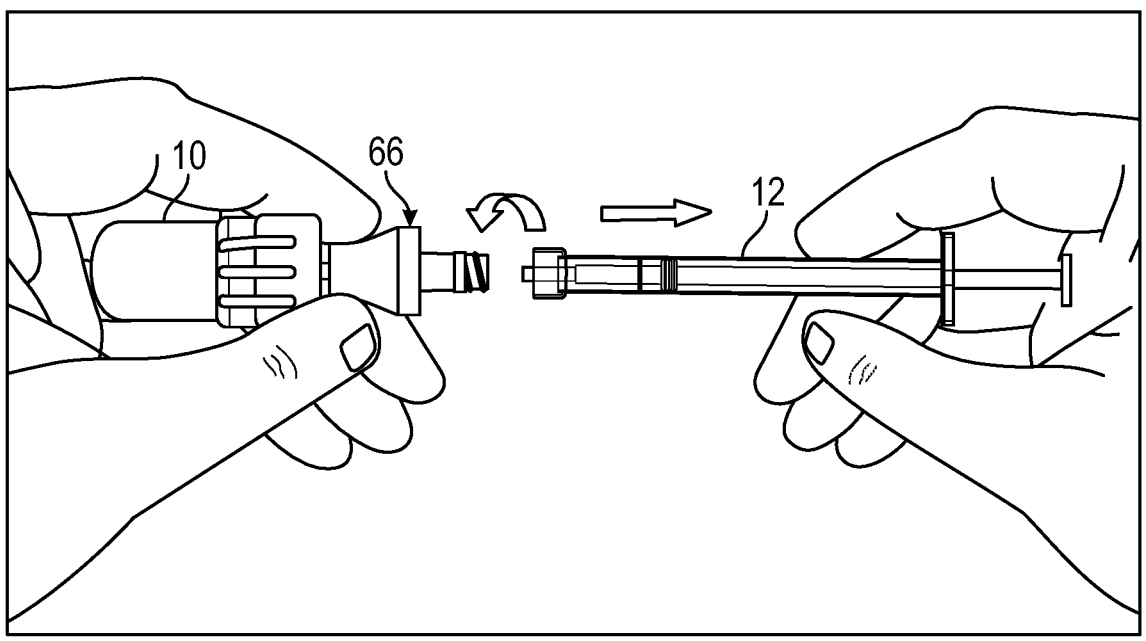

Further provided herein is a method of preparing a predetermined dose of a pharmaceutical agent for administration to a patient. The method includes providing a system described in Section I, optionally in the form of a kit described in Section II, connecting the plunger rod to the carrier (as shown in FIG. 8A); connecting the safety connector to the syringe end of the vial adapter (as shown in FIG. 8B), thereby opening the check valve in the safety connector and the check valve in the vial adapter; pushing the vial end of the vial adapter onto the sealed container thereby piercing a lid of the sealed container with the spike (as shown in FIG. 8C); injecting the entire sterile diluent from the carrier into the vial via the safety connector and the vial adapter (as shown in FIG. 8D); inverting the sealed container repeatedly to mix the cytotoxic pharmaceutical agent and the sterile liquid to form a reconstituted cytotoxic formulation; disconnecting the safety connector from the vial adapter (as shown in FIG. 8E); connecting the sterile syringe to the syringe end of the vial adapter (as shown in FIG. 8F); and withdrawing a predetermined volume of the reconstituted pharmaceutical agent into the sterile syringe (as shown in FIG. 8G). The method may further include disconnecting the sterile syringe from the vial adapter (as shown in FIG. 8H). The method may further include attaching needle, such as a hypodermic needle or surgical cannula, to the sterile syringe, the needle being suitable to inject the reconstituted pharmaceutical agent. In some examples, the needle may be a 30-gauge needle, a 29 gauge needle, a 27 gauge needle, or a 25 gauge needle. In some embodiments, the method may be performed before, during, or after glaucoma surgery. In some embodiments, the administration by be performed via injection.

The predetermined dose of the pharmaceutical agent and the predetermined volume of the pharmaceutical agent may vary based on the needs of the patient, as will be appreciated by those having skill in the art. The method ensures that an exact dose of the pharmaceutical agent is prepared in a closed system without any exposure to air or to personnel prior to administration to the patient. Those having ordinary skill in the art will further appreciate that the predetermined dose of the pharmaceutical agent may be accurately measured based on the volume of sterile diluent provided in the carrier, the mass of the pharmaceutical agent in the sealed container, and the volume of the reconstituted pharmaceutical agent withdrawn into the sterile syringe. As a non-limiting example, a carrier may be provided with 1 mL of sterile diluent and a sealed container may be provided with 0.2 mg of the pharmaceutical agent. The reconstituted pharmaceutical agent would then have a concentration of 0.2 mg/mL. Therefore, if a 20 µg dose of the pharmaceutical agent is to be administered, a person having ordinary skill in the art would know to withdraw 0.1 mL of the reconstituted pharmaceutical agent intended for injection into the sterile syringe prior to administration. Injection may thus be preferred to use of the sterile, absorbent pads because the amount of drug delivered to the tissue may be determined with greater accuracy.

Further provided herein is a method of treatment, the method including providing a system described in Section I, optionally in the form of a kit described in Section II; connecting the safety connector to the syringe end of the vial adapter, thereby opening the check valve in the safety connector and the check valve in the vial adapter; pushing the vial end of the vial adapter onto the sealed container thereby piercing a lid of the sealed container with the spike; injecting the entire sterile diluent from the carrier into the vial via the safety connector and the vial adapter; inverting the sealed container repeatedly to mix the cytotoxic pharmaceutical agent and the sterile liquid to form a reconstituted cytotoxic formulation; disconnecting the safety connector from the vial adapter; connecting the sterile syringe to the syringe end of the vial adapter; and withdrawing a predetermined volume of the reconstituted pharmaceutical agent into the sterile syringe; disconnecting the sterile syringe from the vial adapter; and administering the reconstituted pharmaceutical agent to the patient.

In some embodiments, the pharmaceutical agent may be administered via injection. In embodiments where the pharmaceutical agent is administered via injection, a needle may be attached to the sterile syringe after disconnecting the sterile syringe from the vial adapter. In some examples, the needle may be a 30-gauge needle. In some aspects, the pharmaceutical agent may be administered via subconjunctival injection, sub-Tenon injection, intra-Tenon injection or episcleral injection. The injection of the pharmaceutical agent may form a bleb. In some examples, the bleb may be shaped and positioned by applying pressure with a wet cotton swab, a blunt tipped instrument, or a Weck-Cel® sponge. This helps to control the amount, location and types of tissue exposed to the pharmaceutical agent. In some aspects, the pharmaceutical agent may be administered via injection into the periocular tissue of the patient. In some aspects, the periocular tissue may include an episcleral (sub-Tenon's) space.

IV. Pharmaceutical Agent in Reconstitutable Form

A sealed container of the present invention refers to any container that is suitable for housing a pharmaceutical agent, which includes at least one pharmaceutically active ingredient (API), and optionally at least one pharmaceutically acceptable excipient. The pharmaceutical agent is in a form ready to be reconstituted, such as in the form of freeze-dried (lyophilized) powder or an API concentrate.

The pharmaceutical agent may include an antimetabolite agent. In some embodiments, the antimetabolite agent may include mitomycin C (MMC), mercaptopurine, fludarabine, fluorouracil, gemcitabine, cytarabine, pemetrexed, methotrexate, capecitabine, hydroxyurea, cladribine, pralatrexate, thioguanine, nelarabine, floxuridine, decitabine, clofarabine, or other antimetabolite agents known in the art and combinations thereof. In a preferred embodiment, the antimetabolite agent is MMC. MMC is commercially available in a lyophilized powder form, which is reconstituted prior to use with normal saline, a balanced salt solution or sterile water. In an exemplary embodiment, the pharmaceutical agent is Mitosol®.

The amount of the pharmaceutical agent in the container can comprise from about 0.01 mg to about 40 mg, from about 0.01 mg to about 0.5 mg, from about 0.5 mg to about 1 mg, from about 1 mg to about 2 mg, from about 2 to about 5 mg, from about 5 to about 7 mg, from about 7 to about 10 mg, from about 10 mg to about 20 mg, from about 20 mg to about 30 mg, or from about 30 mg to about 40 mg. In one embodiment, the pharmaceutical agent is MMC in an amount of 0.01 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, or 40 mg. For example, the container may include 0.2 mg of lyophilized mitomycin-c powder.

Optionally, pharmaceutically acceptable excipients may be admixed with an API in a pharmaceutically acceptable manner. Non-limiting examples of pharmaceutically acceptable excipients include chemical enhancers, cryoprotectants, antioxidants, preservatives, solubilizers, adjuvants, osmotic diuretics, carriers, vehicles, coatings, and any combinations thereof. Optionally, the pharmaceutically acceptable excipients may be preservative-free. One or more excipients can be selected for topical, parenteral, intraperitoneal, intravascular, intramuscular, subcutaneous, subconjunctival and/or sub-Tenon administration.

A. Cryoprotectants

A cryoprotectant is an excipient that prevents damage to API during freezing and drying cycle. Non-limiting examples of cryoprotectants include glycerol, propylene glycol, dimethyl sulfoxide (DMSO).

B. Preservatives

Preservatives are natural or man-made chemicals that may prevent the growth or proliferation of microorganisms in medical or food products. They can be called be called antimicrobials, antioxidants, or even anti-infectives. Sometimes, preservatives may not be desired, due to allergy or other reasons. Thus, "preservative-free" of the pharmaceutical agent is one feature of the instant invention. Non-limiting examples of preservatives include, but are not limited to, ascorbic acid and its salts, ascorbyl palmitate, ascorbyl stearate, anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivatives, vitamin Q10, wheat germ oil, zeaxanthin, or combinations thereof.

C. Dispersants

Dispersants may include but are not limited to starch, alginic acid, polyvinylpyrrolidones, guar gum, kaolin, bentonite, purified wood cellulose, sodium starch glycolate, isoamorphous silicate, and microcrystalline cellulose as high hydrophilic-lipophilic balance (HLB) emulsifier surfactants.

D. pH Modifiers

Non-limiting examples of pH modifiers include hydrochloric acid, citric acid, acetic acid, tartaric acid, malic acid, fumaric acid, lactic acid, phosphoric acid, sorbic acid, benzoic acid, sodium carbonate and sodium bicarbonate.

E. Antimicrobial Agents

An antimicrobial agent may be included as an excipient to minimize the degradation of the compound according to this disclosure by microbial agents, including but not limited to bacteria and fungi. Non-limiting examples of antimicrobials include parabens, chlorobutanol, phenol, calcium propionate, sodium nitrate, sodium nitrite, $Na_2EDTA$, and sulfites including but not limited to sulfur dioxide, sodium bisulfite, and potassium hydrogen sulfite.

F. Osmotic Diuretics

An osmotic diuretic is a type of diuretic that inhibits reabsorption of water and sodium (Na). It is a pharmacologically inert substance that, when used properly, allows appropriate exposure of API to the tissue, so that the maximum bioavailability can be achieved. Examples of osmotic diuretic include mannitol and isosorbide. The pharmaceutical agent of the current invention may comprise excipients of osmotic diuretics, such as mannitol or isosorbide.

EXEMPLARY EMBODIMENTS

Embodiment 1: A sterile, closed system for preparing cytotoxic formulation to body tissue comprising:
 a sealed container of a single dose of a cytotoxic pharmaceutical agent in a reconstitutable form;
 a carrier containing a sterile liquid;
 a safety connector comprising a check valve, the safety connector permanently connected to the carrier; and
 a vial adapter comprising a check valve, a vial end, and a syringe end, the vial adapter operable to removably connect to the sealed container via a spike at the vial end and connect to the safety connector at the syringe end,
 wherein:
 the check valve in the safety connector and the check valve in the vial adapter each open only when the safety connector is properly connected to the vial adapter,
 the carrier is operable to deliver the sterile liquid to the sealed container via the safety connector and the vial adapter and withdraw a cytotoxic formulation comprising a reconstituted mixture of the cytotoxic pharmaceutical agent and sterile liquid, and
 the connections between the carrier, safety connector, and vial adapter remain sterile.

Embodiment 2: The system of embodiment 1, wherein the cytotoxic pharmaceutical agent comprises at least one antimetabolite agent.

Embodiment 3: The system of embodiment 2, wherein the at least one antimetabolite agent is mitomycin-C.

Embodiment 4: The system of embodiment 1, wherein the cytotoxic pharmaceutical agent in a reconstitutable form comprises a lyophilized powder.

Embodiment 5: The system of embodiment 1, wherein the sterile liquid comprises sterile water.

Embodiment 6: The system of embodiment 1, further comprising a tray comprising:
 a compartment with at least one sterile, absorbent pad loosely contained therein; and
 a first cylindrical connector having a first passage that extends between the tray compartment and an exterior of the tray that is communicable with the carrier and safety connector for receiving the cytotoxic formulation,
 wherein the tray is removably connectable to the safety connector via the first cylindrical connector, and
 wherein the pad is removable from the tray compartment for transient application of the cytotoxic formulation to the body tissue.

Embodiment 7: The system of embodiment 1, wherein the at least one sterile absorbent pad comprises an array of pre-cut absorbent pads or sponges with sizes of from 3 to 6 mm, wherein the array comprises at least one rectangle and at least one half-moon and at least one wedge.

Embodiment 8: The system of embodiment 1, wherein the tray has a cover that is movable between opened and closed positions for providing access to the compartment and the pad in the compartment.

Embodiment 9: The system of embodiment 1, further comprising a second sterile syringe, wherein the tray further comprises a second passage and the tray is removably connectable with the second sterile syringe through the second passage.

Embodiment 10: The system of embodiment 9, wherein the second sterile syringe is operable to aspirate air and/or liquid from the compartment by a suction force.

Embodiment 11: A kit for sterile preparation of a cytotoxic formulation comprising:
 a sealed container of a single dose of a cytotoxic pharmaceutical agent in a reconstitutable form;
 a carrier containing a sterile liquid;
 a safety connector comprising a check valve, the safety connector permanently connected to the carrier;
 a vial adapter comprising a check valve, a vial end, and a syringe end, the vial adapter operable to removably connect to the sealed container via a spike at the vial end and connect to the safety connector at the syringe end; and
 a sterile packaging container, the sterile packing container comprising an internal volume that is sealed, the internal volume housing the sealed container, the carrier connected to the safety connector, and the vial adapter in a sterile environment,
 wherein:
 the check valve in the safety connector and the check valve in the vial adapter each open when the safety connector is properly connected to the vial adapter,
 the carrier is operable to deliver the sterile liquid to the sealed container via the safety connector and the vial adapter and withdraw a cytotoxic formulation comprising a reconstituted mixture of the cytotoxic pharmaceutical agent and sterile liquid, and
 the connections between the carrier, safety connector, and vial adapter remain sterile.

Embodiment 12: The kit of embodiment 11, further comprising an instruction slip for user direction.

Embodiment 13: The kit of embodiment 11, further comprising a waste container.

Embodiment 14: The kit of embodiment 11, further comprising a non-sterile outer packaging container.

Embodiment 15: The kit of embodiment 11, wherein the cytotoxic pharmaceutical agent comprises at least one antimetabolite agent.

Embodiment 16: The kit of embodiment 15, wherein the at least one antimetabolite agent is mitomycin-C.

Embodiment 17: The kit of embodiment 11, wherein the cytotoxic pharmaceutical agent in a reconstitutable form comprises a lyophilized powder.

Embodiment 18. The kit of embodiment 11, wherein the sterile liquid comprises sterile water.

Embodiment 19. The kit of embodiment 11, further comprising a tray comprising:
- a compartment with at least one sterile, absorbent pad loosely contained therein; and
- a first passage that extends between the tray compartment and an exterior of the tray that is communicable with the carrier and safety connector for receiving the cytotoxic formulation,
- wherein the tray is removably connectable with the safety connector through the first passage, and
- wherein the pad is removable from the tray compartment for transient application of the cytotoxic formulation to the body tissue.

Embodiment 20: The kit of embodiment 11, wherein the at least one sterile absorbent pad comprises an array of pre-cut absorbent pads or sponges with sizes of from 3 to 6 mm, wherein the array comprises at least one rectangle and at least one half-moon and at least one wedge.

Embodiment 21: The kit of embodiment 11, wherein the tray has a cover that is movable between opened and closed positions for providing access to the compartment and the pad in the compartment.

Embodiment 22: The kit of embodiment 11, further comprising a sterile syringe, wherein the tray further comprises a second cylindrical connector having a second passage and the tray is removably connectable with the sterile syringe via the second cylindrical connector.

Embodiment 23. The kit of embodiment 22, wherein the sterile syringe is operable to aspirate air and/or liquid from the compartment by a suction force.

Embodiment 24. A method of preparing a cytotoxic formulation for administration to a tissue, comprising:
providing a sterile, closed system, comprising:
- a sealed container of a single dose of a cytotoxic pharmaceutical agent in a reconstitutable form;
- a carrier containing a sterile liquid;
- a safety connector comprising a check valve, the safety connector permanently connected to the carrier; and
- a vial adapter comprising a check valve, a vial end, and a syringe end, the vial adapter operable to removably connect to the sealed container via a spike at the vial end and connect to the safety connector at the syringe end;

connecting the safety connector to the syringe end of the vial adapter, thereby opening the check valve in the safety connector and the check valve in the vial adapter;

pushing the vial end of the vial adapter onto the sealed container, thereby piercing a lid of the sealed container with the spike;

injecting the entire sterile water from the carrier into the vial, via the safety connector and the vial adapter;

inverting the sealed container repeatedly to mix the cytotoxic pharmaceutical agent and sterile liquid to form a reconstituted cytotoxic formulation;

withdrawing a volume of the cytotoxic formulation back into the carrier; and disconnecting the safety connector from the vial adapter, thereby closing the check valve in the safety connector and closing the check valve in the vial adapter, wherein the safety connector remains connected to the carrier and the vial adapter remains connected to the sealed container.

Embodiment 25: The method of embodiment 24, wherein the cytotoxic pharmaceutical agent comprises at least one antimetabolite agent.

Embodiment 26: The method of embodiment 25, wherein at least one antimetabolite agent is mitomycin-C.

Embodiment 27: The method of embodiment 26, wherein the concentration of the cytotoxic formulation withdrawn into the carrier is at least 0.1 mg/mL mitomycin C.

Embodiment 28: The method of embodiment 24, further comprising:
- connecting the safety connector to a first passage of a tray comprising a compartment with at least one sterile, absorbent pad loosely contained therein; and
- connecting a second sterile syringe to a second passage of the tray.

Embodiment 29: The method of embodiment 28, further comprising:
- injecting the volume of the cytotoxic formulation in the carrier into the compartment of the tray, thereby saturating the at least one sterile, absorbent pad; and
- withdrawing any excess cytotoxic formulation and/or air into the second sterile syringe.

Embodiment 30: A method of administering a cytotoxic formulation to a tissue, the method comprising:
- preparing the cytotoxic formulation according to claim 29;
- removing one or more saturated sterile, absorbent pads from the compartment of the tray; and
- applying the one or more saturated sterile, absorbent pads to the tissue.

Embodiment 31: The method of embodiment 30, further comprising removing the one or more saturated sterile, absorbent pads from the tissue after a period of time.

Embodiment 32: The method of embodiment 31, wherein the period of time is 2 minutes.

Embodiment 33: The method of embodiment 30, wherein the tissue is periocular tissue.

Embodiment 34: The method of embodiment 33, further comprising performing a peritomy after removing one or more saturated sterile, absorbent pads.

Embodiment 35: The method of embodiment 33, wherein the periocular tissue receives at least 0.1 mL of the cytotoxic formulation via the one or more saturated sterile, absorbent pads.

Embodiment 36: The method of embodiment 33, wherein the periocular tissue comprises an episcleral (sub-Tenon's) space.

Embodiment 37: The method of embodiment 33, wherein the cytotoxic formulation is applied to the periocular tissue prior to, during, or after an ophthalmic surgical procedure.

Embodiment 38: A method of preparing a cytotoxic formulation for administration to a tissue, the method comprising:
providing a sterile, closed system, comprising:
- a sealed container of a single dose of a cytotoxic pharmaceutical agent in a reconstitutable form;
- a carrier containing a sterile liquid;
- a safety connector comprising a check valve, the safety connector permanently connected to the carrier;
- a vial adapter comprising a check valve, a vial end, and a syringe end, the vial adapter operable to removably connect to the sealed container via a spike at the vial end and connect to the safety connector at the syringe end; and a sterile syringe operable to connect to the vial adapter;

connecting the safety connector to the syringe end of the vial adapter, thereby opening the check valve in the safety connector and the check valve in the vial adapter;

pushing the vial end of the vial adapter onto the sealed container, thereby piercing a lid of the sealed container with the spike;

injecting the entire sterile water from the carrier into the vial, via the safety connector and the vial adapter;

inverting the sealed container repeatedly to mix the cytotoxic pharmaceutical agent and sterile liquid to form a reconstituted cytotoxic formulation;

disconnecting the vial adapter from the safety connector;

connecting the sterile syringe to the vial adapter; and withdrawing a predetermined volume of the reconstituted cytotoxic formulation into the sterile syringe.

Embodiment 39: The method of embodiment 38, wherein the administration is performed via injection.

Embodiment 40: The method of embodiment 38, wherein the predetermined volume is less than or equal to 1 mL.

Embodiment 41: The method of embodiment 40, wherein the predetermined volume is 0.1 mL.

Embodiment 42: The method of embodiment 38, wherein the reconstituted cytotoxic formulation has a concentration of about 0.01 mg/mL to about 1 mg/m L.

Embodiment 43: The method of embodiment 42, wherein the reconstituted cytotoxic formulation has a concentration of 0.2 mg/m L.

Embodiment 44: The method of embodiment 38, wherein the pharmaceutical agent comprises at least one antimetabolite agent.

Embodiment 45: The method of embodiment 44, wherein at least one antimetabolite agent is mitomycin-C.

Embodiment 46: The method of embodiment 38, further comprising disconnecting the sterile syringe from the vial adapter.

Embodiment 47: The method of embodiment 46, further comprising attaching a needle to the sterile syringe.

Embodiment 48: The method of embodiment 47, further comprising injecting the reconstituted cytotoxic formulation to the periocular tissue of a patient.

Embodiment 49. A method of treating glaucoma, the method comprising:

providing a sterile, closed system, comprising:
a sealed container of a single dose of a cytotoxic pharmaceutical agent in a reconstitutable form;
a carrier containing a sterile liquid and connected to a safety connector, the safety connector comprising a check valve, the safety connector permanently connected to the carrier;
a vial adapter comprising a check valve, a vial end, and a syringe end, the vial adapter operable to removably connect to the sealed container via a spike at the vial end and connect to the safety connector at the syringe end; and a sterile syringe operable to connect to the vial adapter;

connecting the safety connector to the syringe end of the vial adapter, thereby opening the check valve in the safety connector and the check valve in the vial adapter;

pushing the vial end of the vial adapter onto the sealed container, thereby piercing a lid of the sealed container with the spike;

injecting the entire sterile water from the carrier into the vial, via the safety connector and the vial adapter;

inverting the sealed container repeatedly to mix the cytotoxic pharmaceutical agent and sterile liquid to form a reconstituted cytotoxic formulation;

disconnecting the vial adapter from the safety connector;

connecting the sterile syringe to the vial adapter;

withdrawing a predetermined volume of the reconstituted cytotoxic formulation into the sterile syringe;

disconnecting the sterile syringe from the vial adapter;

attaching a needle to the sterile syringe; and injecting the reconstituted cytotoxic formulation to the periocular tissue of a patient in need thereof.

Embodiment 50: The method of embodiment 49, wherein the predetermined volume is less than or equal to 1 mL.

Embodiment 51: The method of embodiment 50, wherein the predetermined volume is 0.1 mL.

Embodiment 52: The method of embodiment 49, wherein the reconstituted cytotoxic formulation has a concentration of about 0.01 mg/mL to about 1 mg/mL.

Embodiment 53: The method of embodiment 52, wherein the reconstituted cytotoxic formulation has a concentration of 0.2 mg/mL.

Embodiment 54: The method of embodiment 49, wherein the pharmaceutical agent comprises at least one antimetabolite agent.

Embodiment 55: The method of embodiment 54, wherein at least one antimetabolite agent is mitomycin-C.

Embodiment 56: A method of treating glaucoma, the method comprising:

preparing a reconstituted cytotoxic pharmaceutical formulation in a sterile, closed system; and administering a predetermined volume of the reconstituted cytotoxic pharmaceutical formulation to a patient in need thereof.

Embodiment 57: The method of embodiment 56, wherein the sterile, closed system comprises:

a sealed container of a single dose of a cytotoxic pharmaceutical agent in a reconstitutable form;
a carrier containing a sterile liquid and connected to a safety connector, the safety connector comprising a check valve, the safety connector permanently connected to the carrier;
a vial adapter comprising a check valve, a vial end, and a syringe end, the vial adapter operable to removably connect to the sealed container via a spike at the vial end and connect to the safety connector at the syringe end; and
a sterile syringe operable to connect to the vial adapter.

Embodiment 58: The method of embodiment 56, wherein the reconstituted cytotoxic pharmaceutical formulation comprises an antimetabolite agent.

Embodiment 59: The method of embodiment 56, wherein the predetermined volume is less than or equal to 1 mL.

Embodiment 60: The method of embodiment 59, wherein the predetermined volume is 0.1 mL.

Embodiment 61: The method of embodiment 56, wherein the reconstituted cytotoxic formulation has a concentration of about 0.01 mg/mL to about 1 mg/m L.

Embodiment 62: The method of embodiment 61, wherein the reconstituted cytotoxic formulation has a concentration of 0.2 mg/m L.

Embodiment 63: The method of embodiment 56, wherein the pharmaceutical agent comprises at least one antimetabolite agent.

Embodiment 64: The method of embodiment 63, wherein at least one antimetabolite agent is mitomycin-C.

EXAMPLES

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1. Study Design and Methodology

A clinical study was set up to compare the efficacy and safety of subtenon injection of mitomycin C (MMC) using the instant injection system and kits, with that of conventional application of MMC-soaked sponges in trabeculectomy. Glaucoma patients were randomized into two groups; group 1 received a subtenon injection of 0.1 mL of 0.01% MMC by the second sterile syringe, while group 2 received 0.02% MMC-soaked Weck-Cel® sponges to physically disperse the MMC. The injection was placed in the far posterior fornix on a 30-gauge needle prior to the conjunctival peritomy for trabeculectomy. Primary outcome measure is intraocular pressure (IOP), and secondary outcome measures are endothelial cell count (ECC) changes and bleb morphology according to the Indiana Bleb Appearance Grading Scale. Outcome measures were compared at 1, 3 and 6 months postoperatively. Complete and qualified success was defined as IOP within 6-15 mm Hg without and with medications at month 6, respectively.

Data was to be presented in the form of mean, SD, median and range, frequency and percentage values. Normal distribution of data was assessed by Kolmogrov-Smirnov test and Q-Q plot. To evaluate differences between the study groups, $x2$, t-test and Mann-Whitney tests. Wilcoxon singed-rank test and the linear mixed model were used to assess changes within the study groups. The Wilcoxon singed-rank test is followed by Bonferroni correction to consider multiple comparisons. To compare the groups adjusted for baseline values, analysis of covariance and Poisson regression (based on the type of response) were used. All statistical analyses were performed using SPSS software (IBM SPSS Statistics for Windows, V. 23.0, Released 2014, IBM, Armonk, N.Y., USA.). All tests were two-sided and p values less than 0.05 were considered statistically significant.

Meanwhile, to evaluate the operability and ease of use on the instant injection apparatus and kits, a physician questionnaire was distributed to all participating medical staff right after the use of the instant injection system and kits. The questionnaire included questions on the ease of mixing, the time spent on reconstitution, the time and ease of withdrawing reconstituted pharmaceutical to the sterile syringe, and the handle-ability of the system and kits.

Example 2. Study Results

When compared to cellulose sponge delivery, injecting MMC using the instant invention leads to a lower IOP, a decreased dependence on glaucoma medications, and a more favorable bleb morphology (low and diffuse) when compared to trabeculectomies performed with sponges. Thus, the study points to non-inferiority with improved predictability of MMC injection achieved through the use of the instant apparatus and kits.

In response to the questionnaire, a majority of users gave positive feedback. The users preferred the quick and easy reconstitution, the lessened risk posed by contact, vapor and aerosol hazards, and the rapid, reliable and contained transfer to the sterile syringe.

Example 3: Exemplary Instructions for Use of a Kit of the Present Disclosure 1. Getting Started. Non-sterile Circulating Nurse: Open outer pack. Affect sterile transfer of all contents to the sterile field. Sterile Surgical Technician: Open sterile inner tray.

Figure 7A:
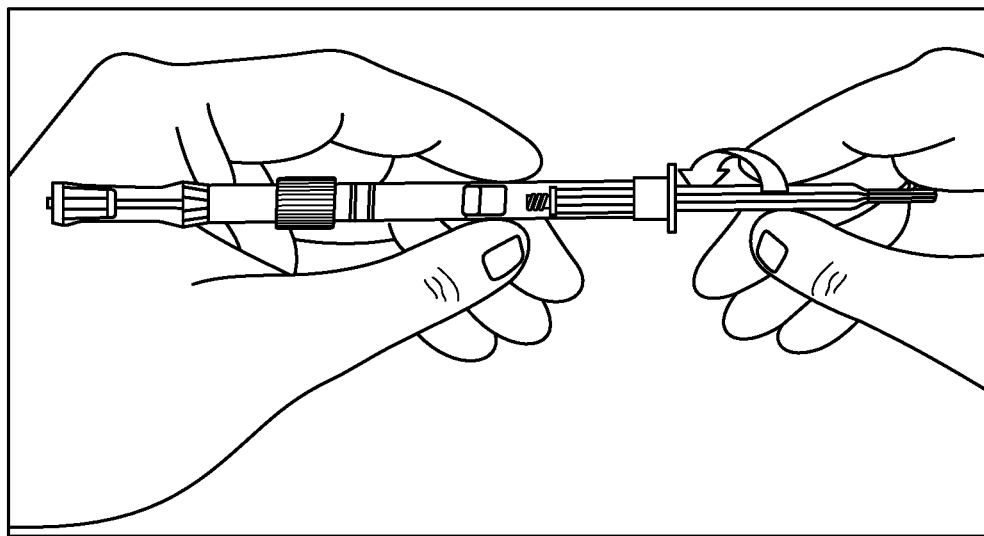
FIGS. 7A-7H show diagrams for using the system of the present disclosure to prepare sponges saturated with the reconstituted pharmaceutical agent.
Figure 7B:
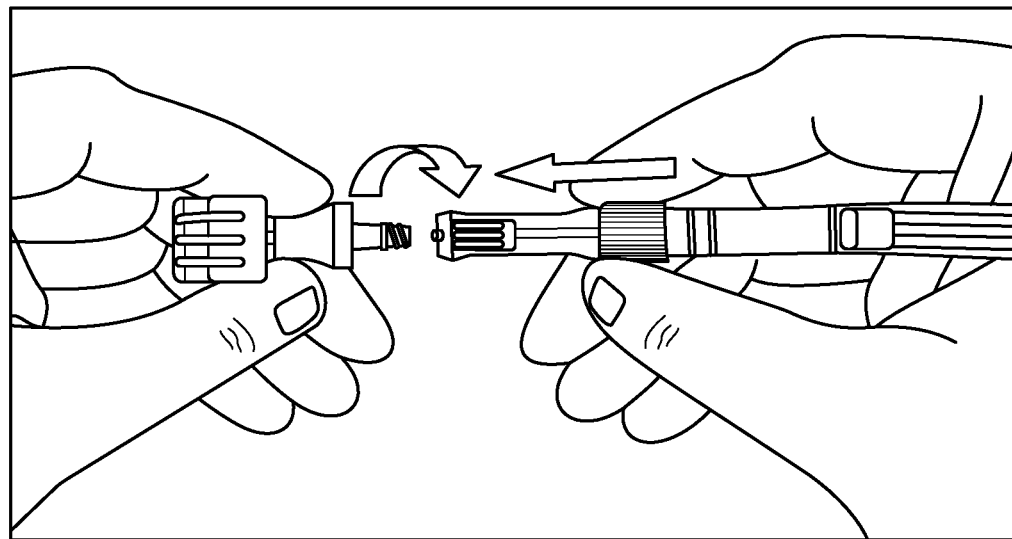

2. Reconstituting the Pharmaceutical Agent. Remove vial and vial adapter from foam pouch. Screw plunger rod to rubber plunger of pre-filled carrier (FIG. 7A). Press firmly and screw the vial end of the vial adapter into the distal end of the safety connector (FIG. 7B).

NOTE: Do not force plunger. Carrier will not operate if vial adapter and safety connector are not properly connected. Forcing plunger may result in syringe leakage and Mitosol® exposure.

Figure 7C:
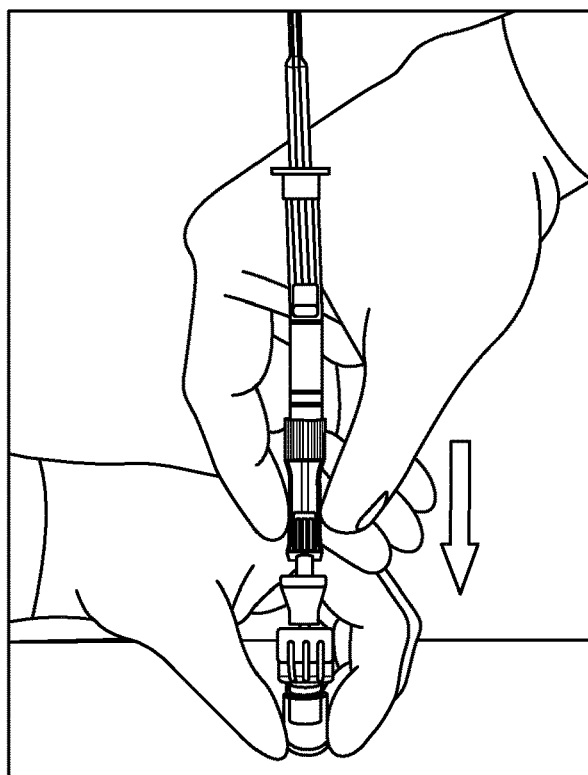
Figure 7D:
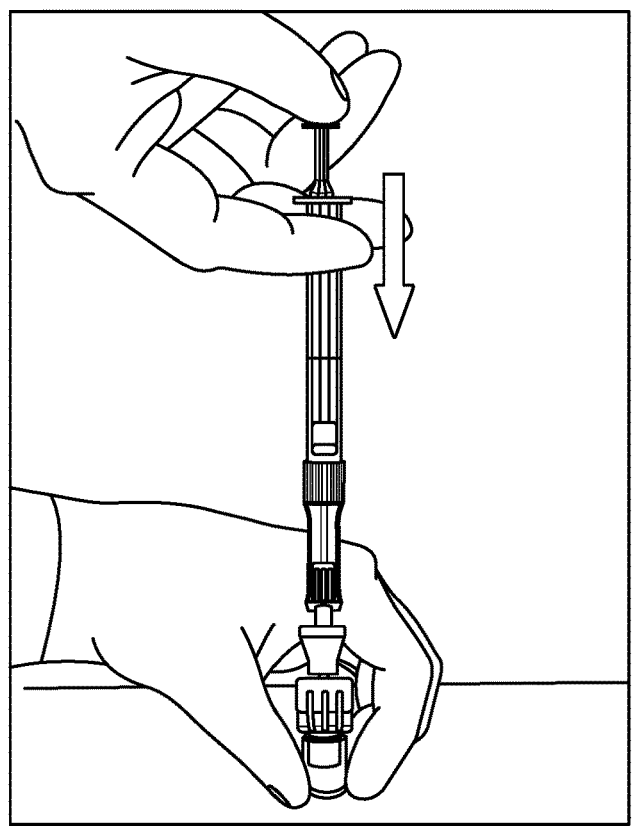

Stand vial upright on a sturdy, flat surface and push on the vial lid until seated and secure (FIG. 7C). Inject the entire contents of sterile water (1 mL) into the vial (FIG. 7D). Do not force carrier plunger (see note).

IMPORTANT: INVERT VIAL REPEATEDLY to saturate ALL drug product, including that adhering to the stopper, then shake until complete reconstitution of Mitosol®. If product does not dissolve immediately, allow to stand at room temperature until the product has dissolved into solution.

Figure 7E:
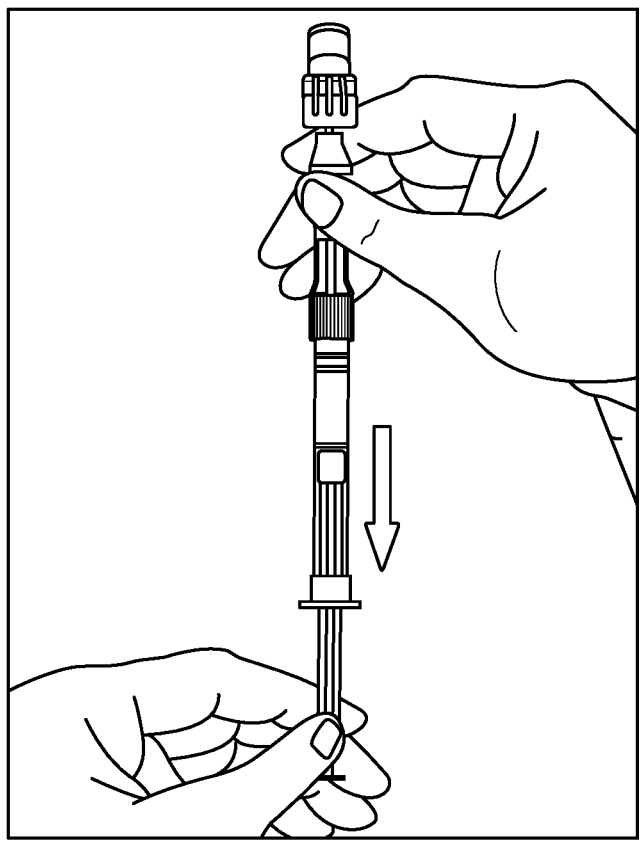
Figure 7F:
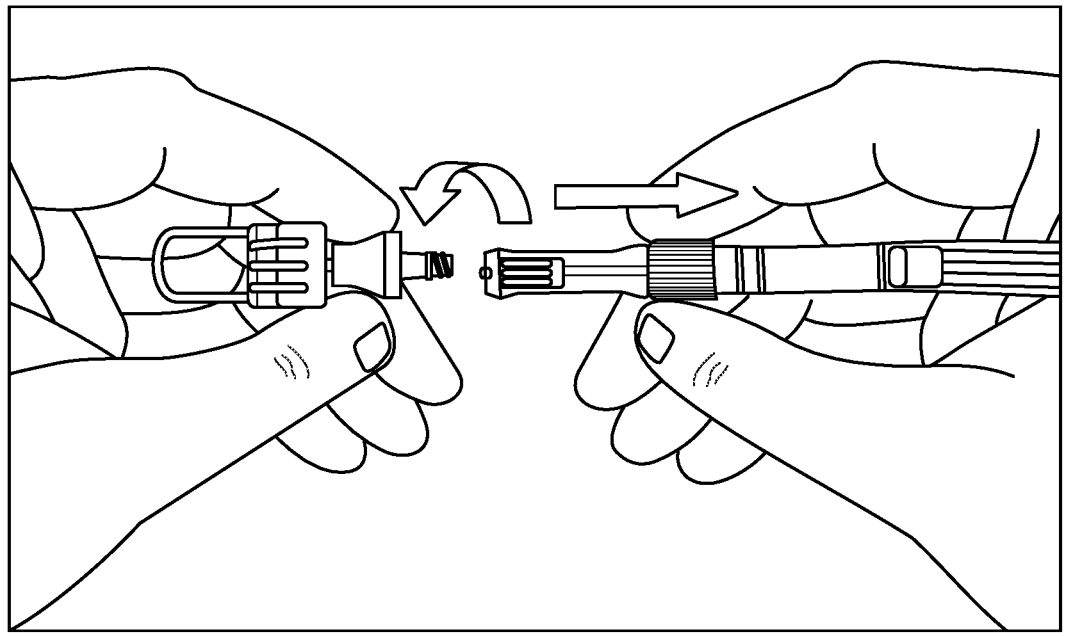

3. Preparing sponges. Invert the vial and carrier and draw full volume of medication into syringe (FIG. 7E). Remove all sponges from sponge tray. Return to sponge tray only those sponges to be saturated with Mitosol®. Unscrew the carrier with safety connector from the vial and vial adapter (FIG. 7F). Note: DO NOT remove safety connector from the carrier.

Figure 7G:
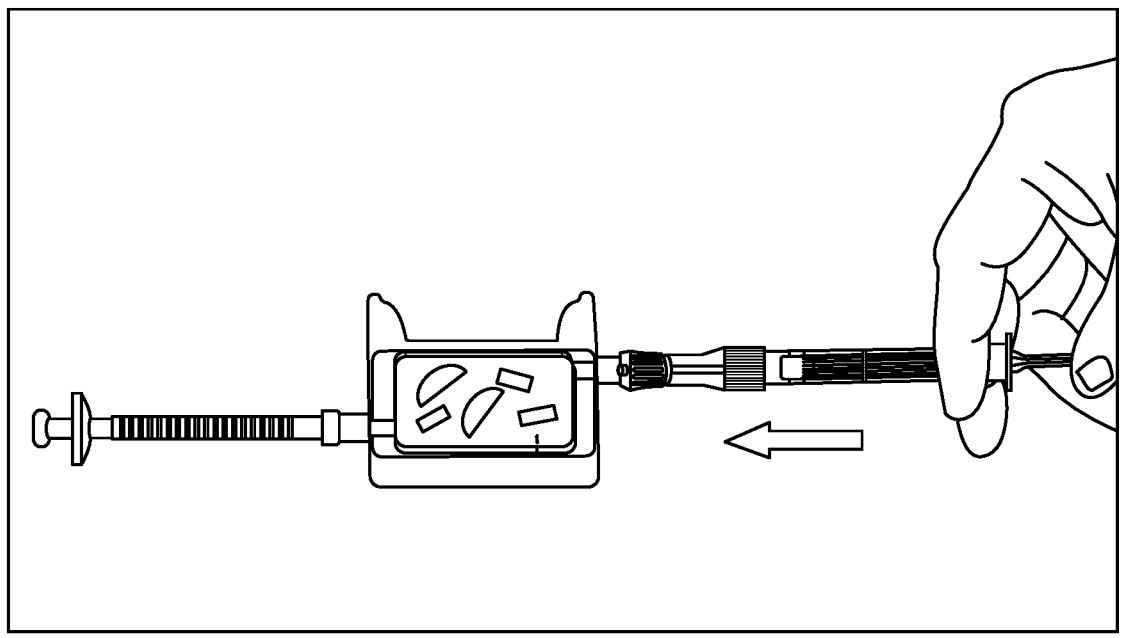

Place vial and vial adapter in chemotherapy waste disposal bag and set aside, within sterile field, for additional use. Take sponge container from sterile inner tray. Screw carrier and TB syringe into sponge container; the TB syringe to one end, the carrier with reconstituted Mitosol® to the other. Mitosol® must be used within 1 hour of reconstitution. Inject medication into sponge container, saturating sponges. Reconstituted Mitosol® should remain undisturbed in sponge container for 60 seconds (FIG. 7G). Do not force carrier plunger, see note at step 2. If any excess fluid remains, withdraw plunger of TB syringe, drawing excess fluid/air into syringe.

Figure 7H:
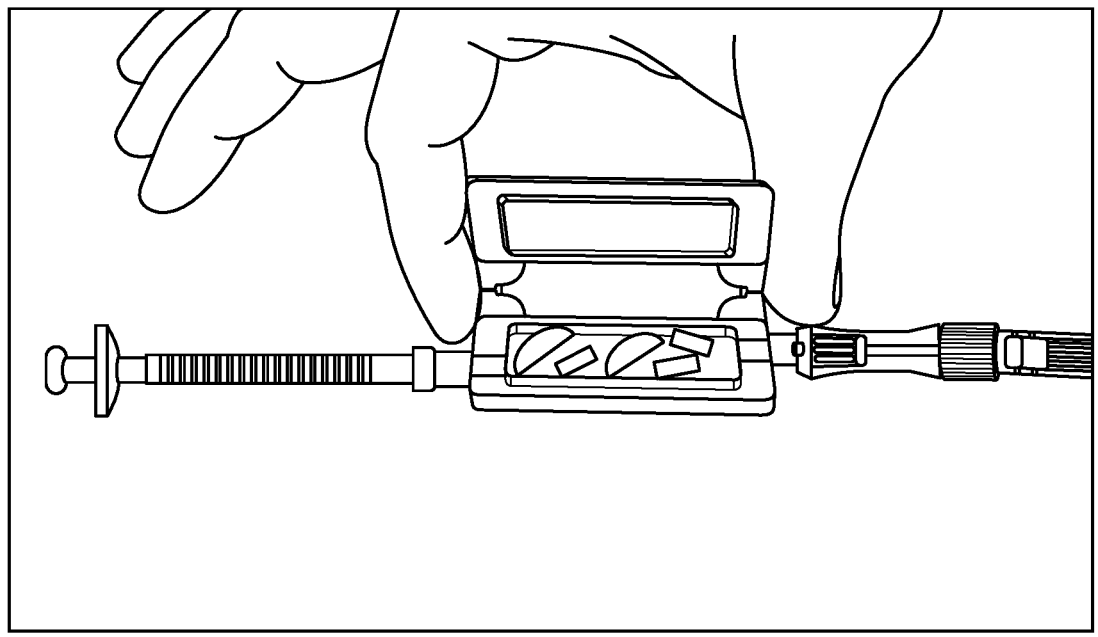

4. Using Mitosol®. With the syringe and carrier connected, the TB syringe to one end, the carrier to the other, open sponge container, offering contents to surgeon for placement on surgical sight (FIG. 7H).

Apply saturated sponges to surgical site for two minutes. Remove sponges from eye and copiously irrigate surgical sight. As used sponges are removed from surgical site, accept used sponges back into sponge container for disposal. Close container lid.

With syringes still connected to sponge container, remove entire assembly from surgical field in chemotherapy waste disposal bag. Dispose of chemotherapy waste bag and its contents as chemotherapy waste.

What is claimed is:

1. A method of preparing a cytotoxic formulation for administration to a tissue, the method comprising:
  providing a sterile, closed system, comprising:
    a sealed container of a single dose of a cytotoxic pharmaceutical agent in a reconstitutable form;
    a carrier containing a sterile liquid;
    a safety connector comprising a check valve, the safety connector permanently connected to the carrier;
    a vial adapter comprising a check valve, a vial end, and a syringe end, the vial adapter operable to removably connect to the sealed container via a spike at the vial end and connect to the safety connector at the syringe end; and
    a sterile syringe operable to connect to the vial adapter;
  connecting the safety connector to the syringe end of the vial adapter, thereby opening the check valve in the safety connector and the check valve in the vial adapter;
  pushing the vial end of the vial adapter onto the sealed container, thereby piercing a lid of the sealed container with the spike;
  injecting the entire sterile water from the carrier into the vial, via the safety connector and the vial adapter;
  inverting the sealed container repeatedly to mix the cytotoxic pharmaceutical agent and sterile liquid to form a reconstituted cytotoxic formulation;
  disconnecting the vial adapter from the safety connector;
  connecting the sterile syringe to the vial adapter; and
  withdrawing a predetermined volume of the reconstituted cytotoxic formulation into the sterile syringe.

2. The method of claim 1, wherein the administration is performed via injection.

3. The method of claim 1, wherein the predetermined volume is less than or equal to 1 mL.

4. The method of claim 3, wherein the predetermined volume is 0.1 mL.

5. The method of claim 1, wherein the reconstituted cytotoxic formulation has a concentration of about 0.01 mg/mL to about 1 mg/mL.

6. The method of claim 5, wherein the reconstituted cytotoxic formulation has a concentration of 0.2 mg/mL.

7. The method of claim 1, wherein the pharmaceutical agent comprises at least one antimetabolite agent.

8. The method of claim 7, wherein at least one antimetabolite agent is mitomycin-C.

9. The method of claim 1, further comprising disconnecting the sterile syringe from the vial adapter.

10. The method of claim 9, further comprising attaching a needle to the sterile syringe.

11. The method of claim 10, further comprising injecting the reconstituted cytotoxic formulation to the periocular tissue of a patient.

12. A method of treating glaucoma, the method comprising:
  providing a sterile, closed system, comprising:
    a sealed container of a single dose of a cytotoxic pharmaceutical agent in a reconstitutable form;
    a carrier containing a sterile liquid and connected to a safety connector, the safety connector comprising a check valve, the safety connector permanently connected to the carrier;
    a vial adapter comprising a check valve, a vial end, and a syringe end, the vial adapter operable to removably connect to the sealed container via a spike at the vial end and connect to the safety connector at the syringe end; and
    a sterile syringe operable to connect to the vial adapter;
  connecting the safety connector to the syringe end of the vial adapter, thereby opening the check valve in the safety connector and the check valve in the vial adapter;
  pushing the vial end of the vial adapter onto the sealed container, thereby piercing a lid of the sealed container with the spike;
  injecting the entire sterile water from the carrier into the vial, via the safety connector and the vial adapter;
  inverting the sealed container repeatedly to mix the cytotoxic pharmaceutical agent and sterile liquid to form a reconstituted cytotoxic formulation;
  disconnecting the vial adapter from the safety connector;
  connecting the sterile syringe to the vial adapter;
  withdrawing a predetermined volume of the reconstituted cytotoxic formulation into the sterile syringe;
  disconnecting the sterile syringe from the vial adapter;
  attaching a needle to the sterile syringe; and
  injecting the reconstituted cytotoxic formulation to the periocular tissue of a patient in need thereof.

13. The method of claim 12, wherein the predetermined volume is less than or equal to 1 mL.

14. The method of claim 13, wherein the predetermined volume is 0.1 mL.

15. The method of claim 12, wherein the reconstituted cytotoxic formulation has a concentration of about 0.01 mg/mL to about 1 mg/mL.

16. The method of claim 15, wherein the reconstituted cytotoxic formulation has a concentration of 0.2 mg/mL.

17. The method of claim 12, wherein the pharmaceutical agent comprises at least one antimetabolite agent.

18. The method of claim 17, wherein at least one antimetabolite agent is mitomycin-C.

19. A method of treating glaucoma, the method comprising:
  preparing a reconstituted cytotoxic pharmaceutical formulation in a sterile, closed system, the closed system comprising:
    a sealed container of a single dose of a cytotoxic pharmaceutical agent in a reconstitutable form,
    a carrier containing a sterile liquid and connected to a safety connector, the safety connector comprising a check valve, the safety connector permanently connected to the carrier,
    a vial adapter comprising a check valve, a vial end, and a syringe end, the vial adapter operable to removably connect to the sealed container via a spike at the vial end and connect to the safety connector at the syringe end, and
    a sterile syringe operable to connect to the vial adapter; and
  administering a predetermined volume of the reconstituted cytotoxic pharmaceutical formulation to a patient in need thereof.

20. The method of claim 19, wherein the reconstituted cytotoxic pharmaceutical formulation comprises an antimetabolite agent.

21. The method of claim 19, wherein the predetermined volume is less than or equal to 1 mL.

22. The method of claim 21, wherein the predetermined volume is 0.1 mL.

23. The method of claim 19, wherein the reconstituted cytotoxic formulation has a concentration of about 0.01 mg/mL to about 1 mg/mL.

24. The method of claim 23, wherein the reconstituted cytotoxic formulation has a concentration of 0.2 mg/mL.

25. The method of claim 19, wherein the pharmaceutical agent comprises at least one antimetabolite agent.

26. The method of claim 25, wherein at least one antimetabolite agent is mitomycin-C.

* * * * *